(12) United States Patent
Okamoto et al.

(10) Patent No.: US 8,084,611 B2
(45) Date of Patent: Dec. 27, 2011

(54) PROCESS FOR PREPARING TETRAHYDROQUINOLINE DERIVATIVES

(75) Inventors: Masaki Okamoto, Osaka (JP); Akira Sakuragi, Osaka (JP); Yoshikazu Mori, Osaka (JP); Takeshi Hamada, Osaka (JP); Hitoshi Kubota, Osaka (JP); Yoshinori Nakamura, Osaka (JP); Takanori Higashijima, Osaka (JP); Norimitsu Hayashi, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 733 days.

(21) Appl. No.: 12/295,618

(22) PCT Filed: Mar. 29, 2007

(86) PCT No.: PCT/JP2007/057610
§ 371 (c)(1),
(2), (4) Date: Sep. 30, 2008

(87) PCT Pub. No.: WO2007/116922
PCT Pub. Date: Oct. 18, 2007

(65) Prior Publication Data
US 2009/0292125 A1 Nov. 26, 2009

(30) Foreign Application Priority Data

Mar. 30, 2006 (JP) .................................. 2006-092783
Nov. 30, 2006 (JP) .................................. 2006-322845

(51) Int. Cl.
*C07D 215/38* (2006.01)
(52) U.S. Cl. ........................................ 546/159; 546/153
(58) Field of Classification Search .................. 546/153, 546/159
See application file for complete search history.

(56) References Cited

U.S. PATENT DOCUMENTS

| 5,576,460 | A | 11/1996 | Buchwald et al. |
| 6,197,786 | B1 | 3/2001 | DeNinno et al. |
| 7,872,125 | B2 * | 1/2011 | Makino et al. .............. 544/284 |

FOREIGN PATENT DOCUMENTS

| EP | 0 386 839 A2 | 3/1990 |
| EP | 0 412 848 A2 | 2/1991 |
| EP | 0 456 442 A1 | 11/1991 |
| EP | 0 495 627 A1 | 7/1992 |
| EP | 0 802 173 A1 | 10/1997 |
| EP | 1 125 929 A1 | 8/2001 |
| EP | 1 318 139 A2 | 6/2003 |
| EP | 1 344 763 A1 | 9/2003 |
| EP | 1 471 050 A1 | 10/2004 |
| EP | 1 533 292 A1 | 5/2005 |
| JP | 3-10056 A | 1/1991 |
| JP | 3-34969 A | 2/1991 |
| JP | 3-161360 A | 7/1991 |
| JP | 3-216566 A | 9/1991 |
| JP | 4-225959 A | 8/1992 |
| JP | 4-312591 A | 11/1992 |
| JP | 5-213884 A | 8/1993 |
| JP | 2001-163859 A | 6/2001 |
| JP | 2004-238322 A | 8/2004 |
| JP | 2004-339205 A | 12/2004 |
| JP | 2005-336083 A | 12/2005 |
| WO | WO-92/22533 A1 | 12/1992 |
| WO | WO-00/17164 A1 | 3/2000 |
| WO | WO-00/17165 A1 | 3/2000 |
| WO | WO-00/17166 A1 | 3/2000 |
| WO | WO-02/088069 A2 | 11/2002 |
| WO | WO-2004/032848 A2 | 4/2004 |
| WO | WO-2004/072041 A1 | 8/2004 |
| WO | WO-2004/074255 A2 | 9/2004 |
| WO | WO-2004/085401 A1 | 10/2004 |
| WO | WO-2005/028419 A2 | 3/2005 |
| WO | WO-2005/095409 A2 | 10/2005 |
| WO | WO-2005/097806 A1 | 10/2005 |
| WO | WO-2006/012093 A1 | 2/2006 |

OTHER PUBLICATIONS

J. G. Tikhe et al., J. Med. Chem., 2004, vol. 47, No. 22, pp. 5467-5481.
D.-M. Cui et al., Tetrahedron Letters, 2003, vol. 44, pp. 4007-4010.
D. B. Damon et al., Organic Process Research & Development, 2006, vol. 10, No. 3, pp. 464-471.
International Preliminary Report on Patentability and Written Opinion corresponding to PCT International Application No. PCT/JP2007/057610 dated Oct. 9, 2008.

* cited by examiner

*Primary Examiner* — D M Seaman
(74) *Attorney, Agent, or Firm* — Birch, Stewart, Kolasch & Birch, LLP

(57) ABSTRACT

The present invention is to provide a process for preparing optically active tetrahydroquinoline derivatives which can be used for the treatment and/or prevention of diseases such as arteriosclerotic diseases, dyslipidemia and the like, and a process for preparing synthetic intermediates thereof.
Specifically, (2R,4S)-2-ethyl-6-trifluoromethyl-1,2,3,4-tetrahydroquinolin-4-ylamine or a salt thereof is prepared with fewer steps without using an optical resolution, and the optically active tetrahydroquinoline derivatives are obtained from the amine compound.

23 Claims, No Drawings

PROCESS FOR PREPARING TETRAHYDROQUINOLINE DERIVATIVES

This Application is the National Phase Under 35 U.S.C. §371 of PCT International Application No. PCT/JP2007/057610 which has an International filing date of Mar. 29, 2007, which claims priority to JP 2006-092783 filed on Mar. 30, 2006 and JP 2006-322845 filed on Nov. 30, 2006.

TECHNICAL FIELD

The present invention relates to processes for preparing tetrahydroquinoline derivatives, which have an inhibitory activity against cholesteryl ester transfer protein (CETP), show effects of increasing HDL cholesterol level and decreasing LDL cholesterol level, and can be used for the treatment and/or prevention of diseases such as arteriosclerotic diseases, hyperlipidemia, dyslipidemia and the like, and also relates to processes for preparing synthetic intermediates thereof.

BACKGROUND ART

CETP inhibitors are effective to inhibit the transfer of cholesteryl ester from HDL to LDL or to VLDL, thereby increasing HDL cholesterol that tends to prevent arteriosclerosis while lowering LDL cholesterol that tends to promote arteriosclerosis, and therefore expected to provide a useful new medical means as a preventive and/or therapeutic agent for arteriosclerotic diseases, hyperlipidemia or dyslipidemia.

And optically active tetrahydroquinoline derivatives are known as CETP inhibitors. See, WO 00/17164, WO 00/17165, WO 00/17166, WO 2006/012093 and WO 2005/095409.

Many of the tetrahydroquinoline derivatives described in the patent literatures above have a common structure of (2R, 4S)-2-ethyl-6-trifluoromethyl-1,2,3,4-tetrahydro-quinolin-4-yl-amine as shown in the formula of I-a:

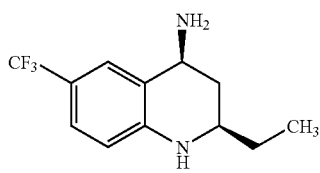

and the compound I-a is considered to be useful as a synthetic intermediate of the optically active tetrahydroquinoline derivatives described above.

Typical methods for preparing the tetrahydroquinoline derivatives are described, for example, in the patent literatures above. For example, optical resolution (Tokkyo Kokai 2001-163859), asymmetric synthesis WO02/088069, and asymmetric synthesis using a ruthenium catalyst (WO2004/074255) are described as a method for preparing optically active tetrahydroquinoline derivatives.

In the methods of preparing optically active tetrahydroquinoline derivatives, there were difficulties due to optical resolution and/or introductions and cleavages of protecting groups. Specifically, an optical resolution is required in a step of preparing the objective compound from 2-ethyl-4-amino-6-trifluoromethyl-1,2,3,4-tetrahydro-quinoline-1-carboxylic acid ethyl ester as shown in the reaction scheme of the patent literature (Tokkyo Kokai 2001-163859).

Moreover, an introduction and cleavage of a protecting group is required in a step of asymmetrical preparation of 4-[acetyl-(3,5-dimethylbenzyl)amino]-2-ethyl-6-trifluoromethyl-3,4-dihydro-2H-quinoline-1-carboxylic acid isopropyl ester from (R)-3-(4-trifluoromethyl-phenylamino)-pentanecarboxylic acid amide as shown in the reaction scheme B of WO 02/088069.

Furthermore, an expensive ruthenium catalyst is required in a step of preparing a compound (5)

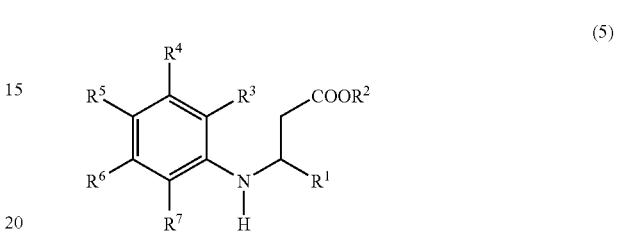

wherein the symbols have the same meaning as defined in WO 2004/074255, by asymmetric reduction of a compound (4)

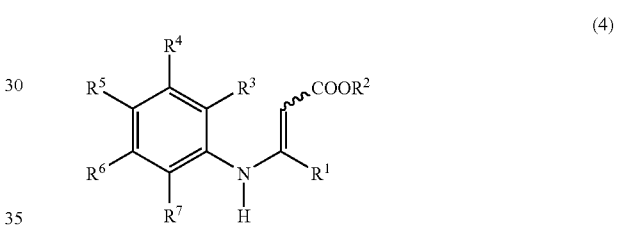

wherein the symbols have the same meaning as defined in WO 2004/074255, and a less expensive process is still desired.

A tetrahydroquinolin-4-one derivative having a similar chemical structure to the compound I-a may be prepared by a cyclization reaction of 3-(2-iodophenylamino)-propionic acid with phosphorus pentoxide, but it could not be prepared with polyphosphoric acid (J. Med. Chem., 47(22), 5467-5481 (2004)). In a case of 4-(4-trifluoromethylphenyl)butyric acid having the trifluoromethyl group at para position of the phenyl ring, however, the similar cyclization reaction did not proceed under the same condition (Tetrahedron Lett., 44, 4007-4010 (2003)).

As a process for preparing a racemate of the compound I-a, WO 00/17164 discloses preparation of a compound V wherein the symbols have the same meaning as defined in WO 00/17164, by reduction of an oxime compound XIII

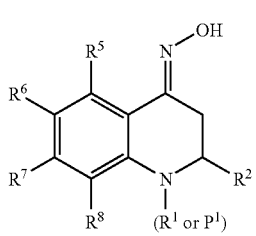

wherein the symbols have the same meaning as defined in WO 00/17164, using Ni—Al alloy. However, a reaction condition of stereoselective reduction is not described.

Additionally, it is known that the tetrahydroquinoline derivative having a similar chemical structure to the compound I-a may be prepared by cyclization reaction of propylidene-(4-trifluoromethyl-phenyl)-amine with a protected vinyl amine as shown in a patent literature (WO 00/17164, Example 7B) and a literature (Organic Process Research & Development 2006, 10, 464-471, Scheme 2). However, a resolution procedure is required at the final step to obtain the optically active tetrahydroquinoline derivative since the cyclization reaction afford a racemic product, and the yield of the optically active tetrahydroquinoline derivative is not satisfactory.

DISCLOSURE OF INVENTION

The present invention is to provide processes for preparing optically active tetrahydroquinoline derivatives which can be used for the treatment and/or prevention of diseases such as arteriosclerotic diseases, hyperlipidemia, dyslipidemia and the like, and to provide processes for preparing synthetic intermediates thereof.

The inventors have extensively studied to find a process for preparing the optically active tetrahydroquinoline derivatives and the compound I-a with fewer steps in which an optical resolution and/or introduction/cleavage of protecting groups is unnecessary.

Moreover, the inventors have extensively studied cyclization reaction of (R)-3-(4-trifluoromethyl-phenylamino)-valeric acid having a trifluoromethyl substituent and no bulky substituent. As a result, they have found out that the cyclization reaction cannot be carried in basic conditions employing butyllithium or in acidic conditions employing methanesulfonic acid or trifluoromethanesulfonic acid, but that it can be carried out in conditions employing both phosphorus pentoxide and methanesulfonic acid.

Furthermore, the inventors have extensively studied stereoselective reduction of (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-methyl-oxime. They have found out that the stereoselective reduction can't be carried out in conditions employing platinum, rhodium, ruthenium, sodium borohydride, lithium aluminum hydride and so on, but that it can be carried out in conditions employing a palladium catalyst, which is advantageous to industrial use, to prepare the compound I-a.

Furthermore, the inventors have extensively studied to find that an asymmetric cyclization reaction of propylidene-(4-trifluoromethyl-phenyl)-amine or an equivalent thereof with optionally protected vinyl amine may be proceeded in the presence of an optically active acid catalyst.

The present invention provides the followings;

1. A process for preparing (2R,4S)-2-ethyl-6-trifluoromethyl-1,2,3,4-tetrahydro-quinolin-4-ylamine shown in the formula I-a:

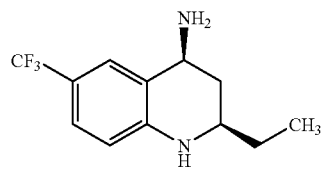

or a salt thereof, comprising catalytic reduction of (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime in the presence of a palladium catalyst, followed by conversion of the product into a salt thereof, if desired.

2. A process for preparing (2R,4S)-2-ethyl-6-trifluoromethyl-1,2,3,4-tetrahydro-quinolin-4-ylamine or a salt thereof, comprising the steps of:

(a) reacting (R)-3-aminovaleric acid or its alkyl ester with a compound of the formula I-f:

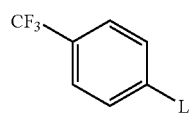

wherein L means a leaving group, to form (R)-3-(4-trifluoromethyl-phenylamino)-valeric acid;

(b) reacting (R)-3-(4-trifluoromethyl-phenylamino)-varelic acid with phosphorus pentoxide to form (R)-2-ethyl-6-trifluoromethyl-2,3-dihydro-1H-quinolin-4-one;

(c) converting (R)-2-ethyl-6-trifluoromethyl-2,3-dihydro-1H-quinolin-4-one into (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime; and (d) carrying out a catalytic reduction of (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime in the presence of a palladium catalyst, followed by conversion of the product into a salt thereof, if desired.

3. A process for preparing (2R,4S)-2-ethyl-6-trifluoromethyl-1,2,3,4-tetrahydro-quinolin-4-ylamine or a salt thereof, comprising asymmetric cyclization reaction of propylidene-(4-trifluoromethyl-phenyl)-amine or its equivalent with an optionally protected vinyl amine shown in the general formula I-g:

wherein R' and R" are the same or different, and hydrogen or an amino-protecting group, or R' and R" combine together to form an amino-protecting group,
in the presence of optically active acid catalyst to prepare a compound of the general formula I-h:

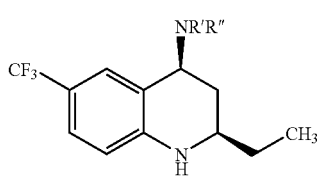

wherein the symbols have the same meaning as above,
and followed by deprotecting the product, if necessary, and converting the product into a salt thereof, if desired.

4. A process for preparing a compound shown in the formula I:

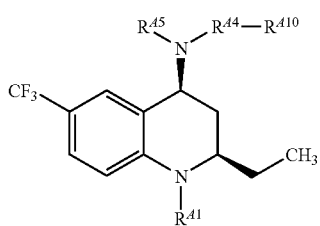

wherein $R^{41}$ is a hydrogen atom, an optionally substituted alkoxycarbonyl group, an optionally substituted carbamoyl group, an optionally substituted alkyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), or a saturated or unsaturated monocyclic or bicyclic heterocyclic carbonyl group containing 1 to 4 heteroatom(s) selected independently from oxygen, sulfur and nitrogen atoms (the heterocyclic group is optionally substituted);
$R^{44}$ is an optionally substituted alkylene group;
$R^{45}$ is a saturated or unsaturated monocyclic or bicyclic heterocyclic group containing 1 to 4 heteroatom(s) selected independently from oxygen, sulfur and nitrogen atoms,
wherein the said heterocyclic group is substituted by 1 to 5 substituent(s) selected from the following groups, or the said heterocyclic group is substituted by 1 to 5 substituent(s) selected from the following groups and further by a halogen atom, an oxo and/or hydroxyl group:
a cyano group, a nitro group, a carboxyl group, a sulfo group, a $C_{3-10}$ alkyl group, a substituted alkyl group, an optionally substituted cycloalkyl group, an optionally substituted alkenyl group, a $C_{3-10}$ alkoxy group, a substituted alkoxy group, an optionally substituted cycloalkoxy group, an optionally substituted alkoxycarbonyl group, an optionally substituted carbamoyl group, an optionally substituted carbamimidoyl group, an optionally substituted alkylthio group, an optionally substituted alkylsulfinyl group, an optionally substituted alkylsulfonyl group, an optionally substituted amino group, an optionally substituted sulfamoyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), a saturated or unsaturated monocyclic or bicyclic heterocyclic oxy group containing 1 to 4 heteroatom(s) selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatom(s) selected independently from oxygen, sulfur and nitrogen atoms (the heterocyclic carbonyl group is optionally substituted); and
$R^{410}$ is an aromatic ring optionally containing 1 to 3 heteroatom(s) selected independently from oxygen, sulfur and nitrogen atoms (the aromatic ring is optionally substituted),
or a pharmaceutically acceptable salt thereof;
comprising preparing (2R,4S)-2-ethyl-6-trifluoromethyl-1,2,3,4-tetrahydroquinolin-4-ylamine or a salt thereof, according to the process of 1, 2 or 3, and introducing —$R^{45}$, —$R^{41}$, and —$R^{44}$—$R^{410}$ respectively, followed by conversion of the product into a pharmaceutically acceptable salt thereof, if desired.

5. A process for preparing a compound shown in the formula I:

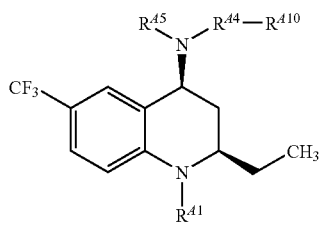

wherein $R^{41}$ is a hydrogen atom, an optionally substituted alkoxycarbonyl group, an optionally substituted carbamoyl group, an optionally substituted alkyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), or a saturated or unsaturated monocyclic or bicyclic heterocyclic carbonyl group containing 1 to 4 heteroatom(s) selected independently from oxygen, sulfur and nitrogen atoms (the heterocyclic group is optionally substituted);
$R^{44}$ is an optionally substituted alkylene group;
$R^{45}$ is a saturated or unsaturated monocyclic or bicyclic heterocyclic group containing 1 to 4 heteroatom(s) selected independently from oxygen, sulfur and nitrogen atoms,
wherein the said heterocyclic group is substituted by 1 to 5 substituent(s) selected from the following groups, or the said heterocyclic group is substituted by 1 to 5 substituent(s) selected from the following groups and further by a halogen atom, an oxo and/or hydroxyl group:
a cyano group, a nitro group, a carboxyl group, a sulfo group, a $C_{3-10}$ alkyl group, a substituted alkyl group, an optionally substituted cycloalkyl group, an optionally substituted alkenyl group, a $C_{3-10}$ alkoxy group, a substituted alkoxy group, an optionally substituted cycloalkoxy group, an optionally substituted alkoxycarbonyl group, an optionally substituted carbamoyl group, an optionally substituted carbamimidoyl group, an optionally substituted alkylthio group, an optionally substituted alkylsulfinyl group, an optionally substituted alkylsulfonyl group, an optionally substituted amino group, an optionally substituted sulfamoyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), a saturated or unsaturated monocyclic or bicyclic heterocyclic oxy group containing 1 to 4 heteroatom(s) selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatom(s) selected independently from oxygen, sulfur and nitrogen atoms (the heterocyclic carbonyl group is optionally substituted); and $R^{410}$ is an aromatic ring optionally containing 1 to 3 heteroatom(s) selected independently from oxygen, sulfur and nitrogen atoms (the aromatic ring is optionally substituted), or a pharmaceutically acceptable salt thereof, comprising preparing (2R,4S)-2-ethyl-6-trifluoromethyl-1,2,3,4-tetrahydroquinolin-4-yl-amine or a salt thereof according to the process of 1, 2 or 3, and introducing —$R^{45}$ at first and then —$R^{41}$ and —$R^{44}$—$R^{410}$ respectively, followed by conversion of the product into a pharmaceutically acceptable salt thereof, if desired.

6. A process for preparing a compound of the general formula II:

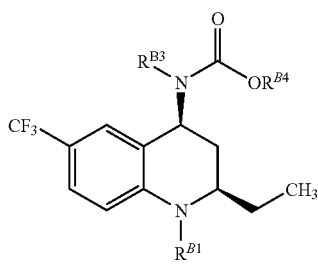

wherein $R^{B1}$ is hydrogen, $Y^B$, $W^B$—$X^B$ or $W^B$—$Y^B$; $W^B$ is carbonyl, thiocarbonyl, sulfinyl or sulfonyl; $X^B$ is —O—$Y^B$, —S—$Y^B$, —N(H)—$Y^B$ or —N($Y^B$)$_2$; and $Y^B$ in each case is independently $Z^B$ or a fully saturated, partially unsaturated or fully unsaturated straight or branched carbon chain having 1 to 10 member(s), wherein the said carbon atom except a linker may be replaced with one or two heteroatom(s) selected independently from oxygen, sulfur and nitrogen; and the said carbon atom may be mono-, di- or tri-substituted with halogen, the said carbon atom may be mono-substituted with hydroxyl and the said carbon atom may be mono-substituted with oxo; the said sulfur may be mono- or di-substituted with oxo; the said nitrogen may be mono- or di-substituted with oxo; and the said carbon chain may be mono-substituted with $Z^B$;

$Z^B$ is a partially saturated, fully saturated or fully unsaturated 3- to 8-membered ring which may contain 1 to 4 heteroatom(s) selected independently from oxygen, sulfur and nitrogen, or a bicyclic ring optionally containing 1 to 4 heteroatom(s) selected independently from nitrogen, sulfur and oxygen, wherein two partially saturated, fully saturated or fully unsaturated 3- to 6-membered rings are fused; and the $Z^B$ group may be substituted independently with 1, 2, or 3 substituent(s) selected from halo, (C$_2$-C$_6$)alkenyl, (C$_1$-C$_6$)alkyl, hydroxyl, (C$_1$-C$_6$)alkoxy, (C$_1$-C$_4$)-alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$)alkylamino; the said (C$_1$-C$_6$)alkyl substituent may be substituted independently with 1, 2, or 3 substituent(s) selected from halo, hydroxyl, (C$_1$-C$_6$)alkoxy, (C$_1$-C$_4$)alkylthio, amino, nitro, cyano, oxo, carboxy, (C$_1$-C$_6$)alkyloxy-carbonyl, mono-N—(C$_1$-C$_6$)alkylamino, and di-N,N—(C$_1$-C$_6$)alkylamino; and the said (C$_1$-C$_6$)alkyl substituent may be substituted with 1- to 9 fluorine;

$R^{B3}$ is hydrogen or $Q^B$; $Q^B$ is a fully saturated, partially unsaturated or fully unsaturated straight or branched carbon chain having 1 to 6 member(s), wherein the carbon atom except a linker may be replaced with one heteroatom selected independently from oxygen, sulfur and nitrogen; and the said carbon atom may be mono-, di- or tri-substituted with halo, the said carbon atom may be mono-substituted with hydroxyl, and the said carbon atom may be mono-substituted with oxo; the said sulfur may be mono- or di-substituted with oxo;

the said nitrogen may be mono- or di-substituted with oxo; and the said carbon chain may be mono-substituted with $V^B$;

$V^B$ is a partially saturated, fully saturated or fully unsaturated 3- to 8-membered ring which may contain 1 to 4 heteroatom(s) selected independently from oxygen, sulfur and nitrogen, or a bicyclic ring optionally containing 1 to 4 hetero-atom(s) selected independently from nitrogen, sulfur and oxygen, wherein two partially saturated, fully saturated or fully unsaturated 3- to 6-membered rings are fused;

the said $V^B$ group may be substituted with 1, 2, or 3 substituent(s) selected from halo, (C$_1$-C$_6$)alkyl, (C$_2$-C$_6$)alkenyl, hydroxyl, (C$_1$-C$_6$)alkoxy, (C$_1$-C$_4$)alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$)alkylamino; the said (C$_1$-C$_6$)alkyl and (C$_2$-C$_6$)alkenyl group may be substituted with 1, 2 or 3 substituent(s) selected from hydroxyl, (C$_1$-C$_6$)alkoxy, (C$_1$-C$_4$)-alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$)alkylamino; the said (C$_1$-C$_6$)alkyl and (C$_2$-C$_6$)alkenyl group may be substituted with 1 to 9 fluorine;

$R^{B4}$ is $Q^{B1}$ or $V^{B1}$; $Q^{B1}$ is a fully saturated, partially unsaturated or fully unsaturated straight or branched carbon chain having 1 to 6 member(s), wherein the carbon atom except a linker may be replaced with one heteroatom selected independently from oxygen, sulfur and nitrogen; and the said carbon may be mono-, di- or tri-substituted with halo, the said carbon may be mono-substituted with hydroxyl, and the said carbon may be mono-substituted with oxo;

the said sulfur may be mono- or di-substituted with oxo;

the said nitrogen may be mono- or di-substituted with oxo; and the said carbon chain may be mono-substituted with $V^{B1}$;

$V^{B1}$ is a partially saturated, fully saturated or fully unsaturated 3- to 6-membered ring which may contain 1 to 2 heteroatom(s) selected independently from nitrogen, sulfur and oxygen; the said $V^{B1}$ group may be substituted with 1, 2, 3 or 4 substituent(s) selected from halo, (C$_1$-C$_6$)alkyl, (C$_1$-C$_6$)alkoxy, amino, nitro, cyano, (C$_1$-C$_6$)alkyloxycarbonyl, mono-N—(C$_1$-C$_6$)alkylamino, and di-N,N—(C$_1$-C$_6$)alkylamino; the said (C$_1$-C$_6$)alkyl group may be mono-substituted with oxo; the said (C$_1$-C$_6$)alkyl group may be substituted with 1 to 9 fluorine; provided that $R^{B3}$ must include $V^B$ or $R^{B4}$ must include $V^{B1}$, a prodrug thereof, or a pharmaceutically acceptable salt of said compound or of said prodrug, comprising preparing (2R,4S)-2-ethyl-6-trifluoromethyl-1,2,3,4-tetrahydroquinolin-4-yl-amine or a salt thereof according to the process of 1, 2, or 3, and introducing —$R^{B1}$, —CO—OR$^{B4}$ and —$R^{B3}$, followed by conversion of the product into a prodrug thereof, or a pharmaceutically acceptable salt of said compound or of said prodrug, if desired.

7. A process for preparing a compound of the general formula III:

[Structure III: 6-CF$_3$-substituted 1,2,3,4-tetrahydroquinoline with N-R$^{C4a}$R$^{C4b}$ at position 4, CH$_2$CH$_3$ at position 2, and N-(CHR$^{C6}$)$_n$-Y$^C$-R$^{C1}$ at position 1]

wherein n is 0, 1, 2 or 3; Y$^C$ is a single bond, C=O or —S(O)$_t$ and t is 0, 1 or 2;

R$^{c1}$ is a group selected from hydroxyl, (C$_1$-C$_6$)alkyl, aryl, (C$_2$-C$_6$)alkenyl, (C$_1$-C$_6$)-haloalkyl, (C$_1$-C$_6$)alkylheterocyclic, (C$_3$-C$_8$)cycloalkyl, (C$_1$-C$_6$)alkylcycloalkyl, (C$_1$-C$_6$) alkylaryl, heterocyclic, (C$_1$-C$_6$)alkylalcohol, (C$_1$-C$_6$)alkoxy, aryloxy, —O(C$_2$-C$_6$)-alkenyl, —O(C$_1$-C$_6$)haloalkyl, —O(C$_1$-C$_6$)alkylheterocyclic, —O(C$_3$-C$_8$)cycloalkyl, —O(C$_1$-C$_6$)alkylcycloalkyl, —NR$^{C7}$R$^{c8}$ and —O(C$_1$-C$_6$) alkylaryl, —O-heterocyclic, —O(C$_1$-C$_6$)alkyl-heterocyclic, (C$_1$-C$_6$)alkyl-O—C(O)NR$^{C7}$R$^{c8}$, (C$_1$-C$_6$)alkyl-NR$^{C7}$C(O)NR$^{C7}$R$^{c8}$, and (C$_0$-C$_6$)alkyl-COOR$^{C11}$;

provided that R$^{c1}$ is not hydroxyl when Y$^C$ is —S(O)$_t$; and the cycloalkyl, the aryl and the heterocyclic may be substituted with 1 to 3 substituent(s) selected independently from oxo, hydroxyl, halo, (C$_1$-C$_6$)alkyl, (C$_2$-C$_6$)alkenyl, (C$_2$-C$_6$)alkynyl, (C$_1$-C$_6$)alkoxy, (C$_1$-C$_6$)haloalkyl, (C$_1$-C$_6$)alkylalcohol, CONR$^{C11}$R$^{12}$, NR$^{C11}$SO$_2$R$^{C12}$, NR$^{C11}$COR$^{C12}$, (C$_0$-C$_3$) alkyl-NR$^{C11}$R$^{C12}$, (C$_1$-C$_3$)alkylCOR$^{C11}$, (C$_0$-C$_6$)alkyl-CO-OR$^{C11}$, cyano, (C$_1$-C$_6$)alkyl-cycloalkyl, phenyl, —O(C$_1$-C$_6$) alkylcycloalkyl, —O(C$_1$-C$_6$)alkylaryl, —O(C$_1$-C$_6$)alkylheterocyclic, and (C$_1$-C$_6$)alkylaryl;

R$^{C4a}$ is a heterocyclic group which is substituted with 1 to 3 substituent(s) selected independently from (C$_3$-C$_6$)alkyl, (C$_3$-C$_6$)alkenyl, (C$_0$-C$_3$)alkyl-CN, (C$_3$-C$_6$)alkoxy, (C$_1$-C$_6$) alkylalcohol, (C$_3$-C$_6$)haloalkyl, —OCONR$^{C11}$R$^{c12}$, (C$_1$-C$_6$) alkyl NR$^{C11}$R$^{C12}$ [the (C$_1$-C$_6$)alkyl may be substituted with —OR$^{C10}$ or —C(O)OR$^{C10}$], (C$_0$-C$_6$)alkyl-NR$^{C11}$SO$_2$R$^{C12}$, (C$_0$-C$_6$)alkyl-C(O)NR$^{C11}$R$^{C12}$, (C$_0$-C$_6$)alkyl-NR$^{c11}$CHR$^{C10}$CO$_2$NR$^{C12}$, (C$_0$-C$_6$)alkyl-NR$^{C11}$C(O)OR$^{C12}$, (C$_0$-C$_6$)alkyl-NR$^{c11}$CHR$^{C10}$CO$_2$NR$^{C12}$, (C$_0$-C$_6$)alkyl-CO(O)R$^{C11}$, (C$_0$-C$_6$)alkyl-SO$_2$NR$^{C11}$R$^{C12}$, (C$_0$-C$_6$)alkyl-SO$_r$R$^{C11}$, (C$_3$-C$_8$)cycloalkyl, (C$_1$-C$_6$)alkyl-cycloalkyl, and (C$_0$-C$_6$)alkylheterocyclic [the heterocyclic ring of the (C$_0$-C$_6$)alkyl-heterocyclic may be substituted with halo, (C$_1$-C$_6$) alkyl, oxo, —CO$_2$R$^{C11}$ or —NR$^{C11}$R$^{C12}$];

R$^{C4b}$ is a group selected from (C$_1$-C$_6$)alkylaryl, (C$_2$-C$_6$)alkenylaryl, (C$_2$-C$_6$)alkynylaryl, (C$_1$-C$_6$)alkylheterocyclic, (C$_2$-C$_6$)alkenylheterocyclic, (C$_1$-C$_6$)alkylcycloalkyl and (C$_1$-C$_6$) alkyl-O—(C$_1$-C$_6$)alkylaryl, and the cycloalkyl, the aryl and the heterocyclic may be substituted with 1 to 3 substituent(s) selected independently from hydroxyl, oxo, —S(C$_1$-C$_6$) alkyl, (C$_1$-C$_6$)alkyl, (C$_2$-C$_6$)alkenyl, (C$_2$-C$_6$)alkynyl, (C$_1$-C$_6$) haloalkyl, a halogen atom, (C$_1$-C$_6$)alkoxy, aryloxy, (C$_2$-C$_6$) alkenyloxy, (C$_1$-C$_6$)haloalkoxyalkyl, (C$_0$-C$_6$)-alkyl-NR$^{C11}$R$^{12}$, —O(C$_1$-C$_6$)alkylaryl, nitro, cyano, (C$_1$-C$_6$) haloalkylalcohol and (C$_1$-C$_6$)alkylalcohol;

R$^{C6}$ is a group selected independently from hydrogen, (C$_1$-C$_6$)alkyl, (C$_2$-C$_6$)alkenyl, hydroxyl, —COR$^{C7}$, (C$_1$-C$_6$) alkoxy, aryloxy, —O(C$_2$-C$_6$)alkenyl, (C$_1$-C$_6$)haloalkyl, (C$_1$-C$_6$)alkyl-NR$^{C7}$R$^{C8}$, (C$_3$-C$_8$)cycloalkyl, heterocyclic, aryl, (C$_1$-C$_6$)alkyl-O—C(O)NR$^{C7}$R$^{C8}$, (C$_1$-C$_6$)alkyl-NR$^{C7}$C(O)NR$^{C7}$R$^{c8}$ and (C$_1$-C$_6$)alkylcycloalkyl, R$^{C7}$ and R$^{C8}$ are groups selected independently from hydrogen, (C$_1$-C$_6$)alkyl, (C$_2$-C$_6$)-alkenyl, (C$_2$-C$_6$)alkynyl, —O(C$_1$-C$_6$)alkyl, (C$_1$-C$_6$)haloalkyl, —O-aryl, —O(C$_3$-C$_8$) cycloalkyl, —O-heterocyclic, —NR$^{C7}$R$^{C8}$, (C$_1$-C$_6$)alkylcycloalkyl, —O(C$_1$-C$_6$)alkylcycloalkyl, —O(C$_1$-C$_6$)alkylheterocyclic, (C$_1$-C$_6$)alkylheterocyclic, —O(C$_1$-C$_6$)alkylaryl, (C$_3$-C$_8$)cycloalkyl, heterocyclic, aryl, and (C$_1$-C$_6$)alkylaryl; and the alkyl, the cycloalkyl, the heterocyclic and the aryl may be substituted with 1 to 3 substituent(s) selected independently from hydroxyl, CN, halo, (C$_1$-C$_6$)alkyl, (C$_1$-C$_6$) alkoxy, (C$_1$-C$_6$)haloalkyl and NR$^{C11}$R$^{C12}$; or R$^{C7}$ and R$^{C8}$ may be combined to form a nitrogen-containing heterocyclic ring further containing 0, 1 or 2 heteroatom(s) selected from an oxygen atom, a nitrogen atom and a sulfur atom, and the said nitrogen-containing heterocyclic ring may be substituted with oxo or (C$_1$-C$_6$)alkyl;

R$^{C10}$, R$^{C11}$ and R$^{C12}$ are groups selected independently from hydrogen, (C$_1$-C$_6$)alkyl, (C$_2$-C$_6$)alkenyl, (C$_3$-C$_8$)cycloalkyl, heterocyclic, aryl and (C$_1$-C$_6$)alkylaryl; and the alkyl, the aryl, the cycloalkyl, and the heterocyclic may be substituted with 1 to 3 substituent(s) selected independently from a halogen atom, (C$_1$-C$_6$)alkylheterocyclic, and (C$_1$-C$_6$)haloalkyl; or R$^{C11}$ and R$^{C12}$ may be combined to form a nitrogen-containing heterocyclic ring further containing 0, 1 or 2 heteroatom(s) selected from an oxygen atom, a nitrogen atom and a sulfur atom; and the said nitrogen-containing heterocyclic ring may be substituted with oxo, (C$_1$-C$_6$)alkyl, —COR$^{C7}$, and —SO$_2$R$^{C7}$;

or a pharmaceutically acceptable salt, solvate, enantiomer, racemate, diastereomer or mixture of diastereomers thereof, comprising preparing (2R,4S)-2-ethyl-6-trifluoromethyl-1,2,3,4-tetrahydroquinolin-4-yl-amine or a salt thereof according to the process of 1, 2 or 3, and introducing —(CHR$^{C6}$)$_n$—Y$^C$—R$^{C1}$, —R$^{C4a}$ and —R$^{C4b}$ respectively, followed by conversion of the product into a pharmaceutically acceptable salt, solvate, enantiomer, racemate, diastereomer or mixture of diastereomers thereof, if desired.

8. A process for preparing (R)-2-ethyl-6-trifluoromethyl-2,3-dihydro-1H-quinolin-4-one comprising reacting phosphorus pentoxide with (R)-3-(4-trifluoro-methyl-phenylamino)-valeric acid.

9. The process of 2, 4, 5, 6, 7 or 8, wherein the reaction of phosphorus pentoxide with (R)-3-(4-trifluoromethyl-phenylamino)-valeric acid is carried out in the presence of an organic sulfonic acid or an organic siloxane.

10. The process of 9, wherein the organic sulfonic acid or the organic siloxane is methanesulfonic acid.

11. The process of 1, 2, 4, 5, 6 or 7, wherein the palladium catalyst is palladium carbon.

12. A process for preparing a compound shown in the general formula I-h:

[Structure I-h: 6-CF$_3$-substituted 1,2,3,4-tetrahydroquinoline with NR'R" at position 4, CH$_2$CH$_3$ at position 2, and NH]

wherein R' and R" are the same or different, and hydrogen or an amino-protecting group, or R' and R" combine together to form an amino-protecting group, comprising asymmetric cyclization reaction of propylidene-(4-trifluoromethyl-phenyl)-amine or an equivalent thereof with an optionally protected vinyl amine shown in the general formula I-g:

I-g wherein the symbols have the same meaning as above, in the presence of an optically active acid catalyst.

13. The process of 3, 4, 5, 6, 7 or 12, wherein R' and R" are the same or different, and hydrogen, a tert-butoxycarbonyl group, a benzyloxycarbonyl group, a 9-fluorenyl-methyloxycarbonyl group, a 2,2,2-trichloroethoxycarbonyl group, a allyloxycarbonyl group, a 1-naphthalenemethoxycarbonyl group, a 2-naphthalenemethoxycarbonyl group, a trifluoroacetyl group, a p-toluenesulfonyl group or a nitrobenzenesulfonyl group; or R' and R" combine together to form a phthaloyl group.

14. The process of 13, wherein R' and R" are the same or different, hydrogen, a benzyloxycarbonyl group, a tert-butoxycarbonyl group, a 1-naphthalenemethoxy-carbonyl group or a 2-naphthalenemethoxycarbonyl group.

15. The process of 3, 4, 5, 6, 7 or 12, wherein the optically active acid catalyst is an optically active Lewis acid catalyst.

16. The process of 15, wherein the optically active Lewis acid catalyst is a compound comprising a Lewis acidic atom and an optically active ligand selected from a biphenol derivative, a 1,1'-binaphthol derivative or an 1,1'-octahydrobinaphthol derivative.

17. The process of 15, wherein the optically active Lewis acid catalyst is a compound comprising an optically active ligand and a Lewis acidic atom, and the optically active ligand is 3,3"-[oxybis(methylene)]bis-(1R,1"R)-1,1'-bi-2-naphthol; (R)-1,1'-binaphthol; (R)-3,3'-dibromo-1,1'-bi-2-naphthol; (R)-6,6'-dibromo-1,1'-bi-2-naphthol; (R)-5,5',6,6',7,7',8,8'-octahydro-bi-2-naphthol; (R)— or (S)-5,5',6,6'-tetramethyl-3,3'-di-tert-butyl-1,1'-biphenyl-2,2'-diol; (R,R)— or (S,S)-1,2-diphenyl-1,2-ethanediol; (1R,2R)- or (1S,2S)-1,2-diphenylethylenediamine; diisopropyl D- or L-tartrate; TADDOL; (R)— or (S)-2-(diphenylhydroxymethyl)pyrrolidine; (R)— or (S)-3-(1H-indol-3-yl)-2-(toluene-4-sulfonylamino)-propionic acid; (R,R)- or (S,S)-2,2'-bis(4-tert-butyl-2-oxazolin-2-yl)propane; (R,R)— or (S,S)-2,2'-bis(4-phenyl-2-oxazolin-2-yl)propane; or (R)— or (S)-2,2'-bis(diphenylphosphino)-1,1-binaphthyl.

18. The process of 15, wherein the optically active Lewis acid catalyst is a compound comprising an optically active ligand and a Lewis acidic atom, and the optically active ligand is 3,3"-[oxybis(methylene)]bis-(1R,1"R)-1,1'-bi-2-naphthol; (R)-1,1'-binaphthol; (R)-3,3'-dibromo-1,1'-bi-2-naphthol; (R)-6,6'-dibromo-1,1'-bi-2-naphthol; (R)-5,5',6,6',7,7',8,8'-octahydro-bi-2-naphthol or (R)-5,5',6,6'-tetramethyl-3,3'-di-tert-butyl-1,1-biphenyl-2,2'-diol.

19. The process of 16, 17 and 18, wherein the Lewis acidic atom is boron, aluminum, titanium or ytterbium.

20. (R)-2-ethyl-6-trifluoromethyl-2,3-dihydro-1H-quinolin-4-one.

21. (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-methyl-oxime.

22. the process of 5, wherein the introduction of —$R^{41}$ and —$R^{44}$—$R^{410}$ is accomplished by introducing —$R^{44}$—$R^{410}$ after the introduction of —$R^{41}$; and 23. the process of 5, wherein the introduction of —$R^{41}$ and —$R^{44}$—$R^{410}$ is accomplished by introducing —$R^{41}$ after the introduction of —$R^{44}$—$R^{410}$.

As used herein, the term "halo", "halogen atom" or "halogen" refers to fluorine, chlorine, bromine or iodine.

The term "alkyl group" or "alkyl" means a straight or branched saturated hydrocarbon chain having 1 to 10 carbon atoms and a cyclic saturated hydrocarbon chain having 3 to 10 carbon atoms. As a straight or branched hydrocarbon chain, those having 2 to 10 carbon atoms are preferred and those having 2 to 6 carbons are more preferred. Other preferred examples are straight or branched chain alkyl groups having 1 to 6 carbon atoms, especially those having 1 to 4 carbon atoms. Examples of alkyl group include methyl, ethyl, propyl, isopropyl, butyl, sec-butyl, tert-butyl, pentyl, isopentyl, neopentyl, tert-pentyl, 1-methylbutyl, 2-methylbutyl, 3-methylbutyl, hexyl and isohexyl groups, and the like.

The term "alkoxy group" or "alkoxy" means a straight or branched alkyloxy group having 1 to 10 carbon atoms and a cyclic alkyloxy group having 3 to 10 carbon atoms. As a straight or branched hydrocarbon chain, those having 2 to 10 carbon atoms are preferred and those having 2 to 6 carbons are more preferred. Other preferred examples are straight chain alkoxy groups having 1 to 6 carbon atoms, especially those having 1 to 4 carbon atoms. Examples of alkoxy group include methoxy, ethoxy, propoxy, isopropoxy, butoxy, isobutoxy, tert-butoxy, pentoxy, isopentoxy, neopentoxy, tert-pentoxy, hexoxy and isohexoxy groups, and the like.

In the present invention, phenyl or naphthyl is typically used as "aryl" or "aryl group".

Reaction Scheme is shown below, wherein the symbols have the same meaning as defined above.

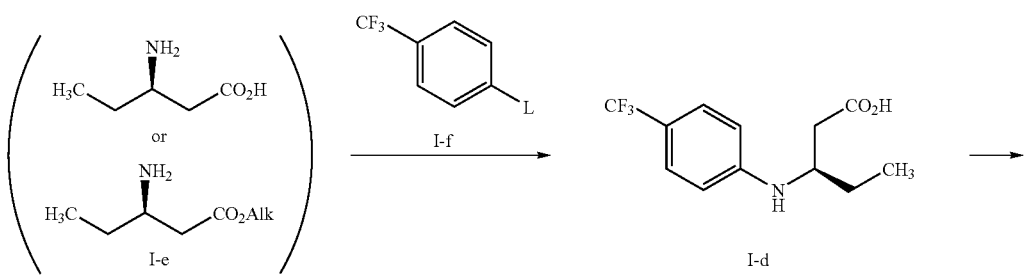

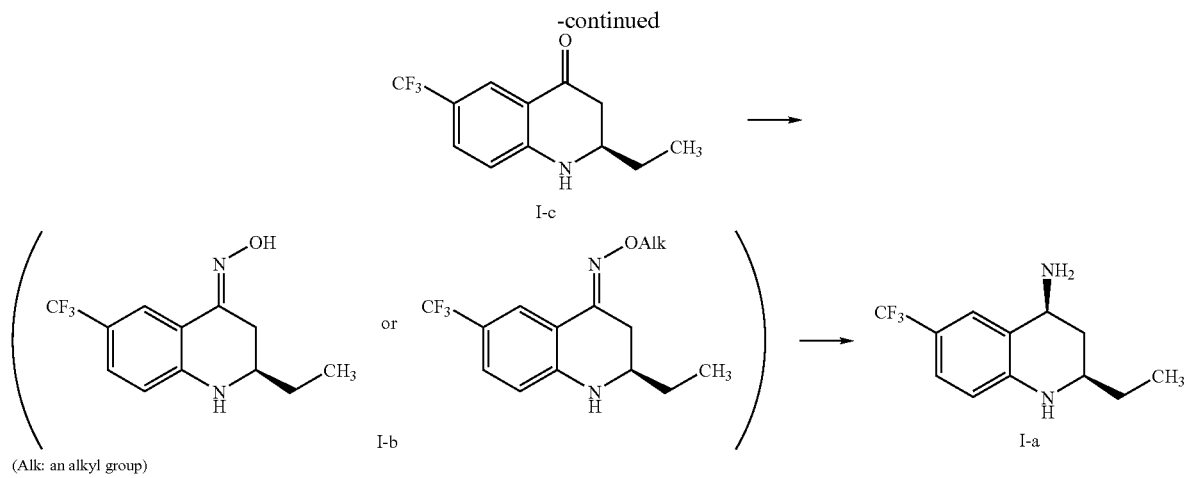

(Alk: an alkyl group)

(1) A Process of Preparing the Compound I-d

The compound I-d can be prepared by reacting the compound I-e with the compound I-f in the presence of a metallic catalyst if desired, in the presence or absence of a base in a suitable solvent.

As to the base for example, alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; alkali metal phosphate including potassium phosphate; amines including triethylamine, diisopropylethylamine, methylpiperidine, dicyclohexylmethylamine; pyridines including pyridine, 4-dimethylaminopyridine can be preferably used.

Additionally, the reaction proceed more preferably when N,N-dimethylform-amide, N,N'-dimethylethylenediamine, 1,10-phenanthroline, ethyleneglycol and/or phenylphenol is added.

Examples of the metallic catalyst include a palladium catalyst and a copper catalyst. As to the palladium catalyst, palladium acetate, tetrakis(triphenylphosphine)palladium, tris (dibenzylideneacetone)dipalladium, dichloro-bis (triphenylphosphine) palladium, dichlorobis(tri-o-tolylphosphine) palladium, bis(triphenylphosphine) palladium acetate and the like can be preferably used. As to the copper catalyst, copper iodide, copper bromide, copper chloride, copper acetate, copper trifluoromethanesulfonate and the like can be preferably used.

Any solvent which dose not disturb the reaction can be preferably used, and examples of such a solvent include water; ethers including diethyl ether, tetrahydrofuran (THF), dioxane, 1,2-dimethoxyethane, diglyme; hydrocarbons including benzene, toluene, hexane, xylene; alcohols including methanol, ethanol, isopropyl alcohol, tert-butanol; esters including ethyl acetate, methyl acetate, butyl acetate; polar solvents including acetone, N,N-dimethylformamide, dimethylsulfoxide and the like, or a mixture thereof. In the present reaction, ethanol, dioxane, toluene, N,N-dimethylformamide and dimethylsulfoxide are preferred.

The leaving group includes a halogen atom including fluorine atom, chlorine atom, bromine atom, iodine atom, and a substituted sulfonyloxy group including methanesulfonyloxy group, p-toluenesulfonyloxy group, trifluoromethanesulfonyloxy group (2) Preparation of the Compound I-c The compound I-c can be prepared by reacting phosphorus pentoxide with the compound I-d, and preferably, the reaction is carried out in the presence of an organic sulfonic acid or organic siloxane together with phosphorus pentoxide.

In the present reaction, phosphorus pentoxide is used as a dehydrating agent.

Examples of the organic sulfonic acid used together with phosphorus pentoxide include a liquid sulfonic acid at room temperature such as aliphatic sulfonic acid or aromatic sulfonic acid, and more specifically, alkylsulfonic acid or benzenesulfonic acid. The more preferable example is $C_{1-4}$ alkylsulfonic acid such as methanesulfonic acid, ethanesulfonic acid, propanesulfonic acid and the like.

Examples of the organic siloxane used in the reaction together with phosphorus pentoxide include a liquid siloxane at room temperature such as polyalkylsiloxane (e.g., hexamethyldisiloxane).

Preferred examples of the organic sulfonic acid include methanesulfonic acid, and preferred examples of the organic siloxane include hexamethyldisiloxane.

In the present invention, Eaton's reagent comprised of phosphorus pentoxide and methanesulfonic acid is most preferable.

In the present reaction, it is essential to use phosphorus pentoxide.

The reaction can be carried out without using a solvent since the organic sulfonic acid or the organic siloxane in the form of a liquid is preferably used together with phosphorus pentoxide. In the process of the present invention, however, a solvent may be additionally used in order to make the handling easier and promote the reaction even if the organic sulfonic acid or the organic siloxane in the form of a liquid is used. A solvent is typically used if the organic sulfonic acid or the organic siloxane is not in the form of a liquid. Examples of the solvent include aromatic hydrocarbons (e.g., benzene, toluene, xylene and the like); halogenated hydrocarbons (e.g., chlorobenzene, trifluoromethylbenzene and the like); ethers (e.g., anisole, diethylglycol, diethyl ether, dimethyl ether and the like); nitriles (e.g., benznitrile and the like); and esters (e.g., butyl acetate and the like). Among them, aromatic hydrocarbons are preferable, and especially toluene or xylene is preferable.

The amount of the dehydrating agent used in the reaction is about 1 to 10 equivalents, preferably about 2 to 4 equivalents per one equivalent of the compound I-d.

The amount of the organic sulfonic acid or the organic siloxane used in the reaction is about 15 to about 40 equivalents, preferably about 20 to about 30 equivalents per one equivalent of the compound I-d.

The reaction can be preferably carried out under heating, at about 50 to about 120° C., preferably about 60 to about 100° C., more preferably about 65 to about 75° C. In the present invention, the reaction time is about 15 minutes to 7 hours, preferably about 2 to 4 hours. The reaction can be carried out with being stirred.

(3) Preparation of the Compound I-b

The compound I-b can be prepared by a conventional method usually used for oxime-preparation, and for example by reacting free hydroxylamine, alkoxyamine or a salt thereof with the compound I-c in a suitable solvent.

When reacting hydroxylamine, hydroxylamine itself or fresh hydroxylamine prepared in situ by neutralization of the hydroxylamine salt in the reaction solvent may be used.

Examples of the hydroxylamine salt include a salt with mineral acids (e.g., hydrochloric acid, sulfuric acid, phosphoric acid, hydrobromic acid, hydroiodic acid and the like), and a salt with organic acids (e.g., acetic acid, oxalic acid, trichloroacetic acid, methanesulfonic acid, p-toluenesulfonic acid, 1,5-naphthalenesulfonic acid and the like).

Any basic substance may be used as a base for neutralizing the hydroxylamine salt, and inorganic bases (e.g., lithium hydroxide, sodium hydroxide, potassium hydroxide, ammonium hydroxide, sodium carbonate, potassium carbonate, sodium bicarbonate and the like), and organic bases (e.g., primary amines including methylamine, ethylamine, aniline; secondary amines including dimethylamine, diethylamine; tertiary amines including triethylamine, trimethylamine, diethylaniline, diisobutylmethylamine; basic heterocycles including pyridine, piperidine, morpholine, 2-methylpyridine, 2,6-lutidine) may be used.

As a hydroxylamine salt, a hydrochloric acid salt and a sulfuric acid salt of hydroxylamine are preferred since they are commercially available.

As a base for neutralizing the hydroxylamine salt, pyridine and sodium acetate and the like are preferred.

Additionally, an aqueous solution of hydroxylamine is also available as a free form thereof. The reaction may be carried out in the aqueous solution.

Any solvent which dissolves hydroxylamine may be used as a solvent, and for example, ethyl acetate, n-heptane, isopropyl alcohol, methanol, ethanol, butanol, methyl cellosolve, ethyl cellosolve, acetone, dioxane, 2-methoxy-propanol, ether, dimethyl-formamide, dimethylacetamide, acetonitrile, tetrahydrofuran, acetic acid, water, and diglyme may be used. Methanol, ethanol, ethyl acetate, n-heptane, isopropyl alcohol, tetrahydrofuran, water, or a mixture thereof is preferable since hydroxylamine does not react with these solvents to give impurities.

The reaction is carried out at −10° C. to 100° C., preferably 0° C. to 60° C., and more preferably 40° C. to 50° C.

As a reaction condition, neutral or basic condition is preferable, and pH range of 7.0 to 14.0, especially pH range of 8.0 to 12.0 is preferable.

(4) A Process of Preparing the Compound I-a or a Salt Thereof

The compound I-a or a salt thereof can be prepared by reducing the compound I-b and followed by converting the product into a salt thereof, if desired.

The reduction is carried out in a suitable solvent under hydrogen atmosphere in the presence of a palladium catalyst.

Examples of the palladium catalyst include palladium carbon, palladium halide such as palladium chloride, organic salt of palladium such as palladium acetate and the like, and palladium carbon is preferable.

The reduction is carried out preferably under medium pressure (1 to 50 atoms), more preferably under 2 to 30 atoms, and most preferably under 5 to 25 atoms.

The reduction is carried out preferably at 0° C. to 80° C., more preferably at 25° C. to 50° C.

Any solvent which dose not disturb the reaction can be preferably used, and examples of such a solvent include ethers including diethyl ether, tetrahydrofuran (THF), dioxane, 1,2-dimethoxyethane, diglyme; hydrocarbons including benzene, toluene, hexane, xylene; alcohols including methanol, ethanol, isopropyl alcohol, tert-butanol; esters including ethyl acetate, methyl acetate, butyl acetate; polar solvents including acetone, N,N-dimethylformamide, dimethylsulfoxide and the like, or a mixture thereof. In the present reaction, ethanol, isopropyl alcohol, dioxane, toluene and N,N-dimethyl-formamide are preferred.

A procedure of forming a salt is easily completed by adding a salt-forming agent. The resulting salt may be obtained by filtration, or recovered by evaporating the solvent.

Any acidic substance may be used as the salt-forming agent, and examples of a suitable salt are reviewed in the literature (Berge et al., J. Pharm. Sci., 66:1-19 (1977)). Examples of the salts include hydrochloride, hydrobromide, hydroiodide, sulfate, bisulfate, nitrate, phosphate, hydrogenphosphate, acetate, maleate, malate, fumarate, lactate, tartrate, citrate, formate, gluconate, succinate, pyruvate, oxalate, oxaloacetate, saccharate, benzoate, methanesulfonate, ethanesulfonate, benzensulfonate, p-toluene-sulfonate and the like.

(5) A Process of Preparing the Compound I

The compound I or a pharmaceutically acceptable salt thereof may be prepared by introducing $—R^{45}$, $—R^{41}$ and $—R^{44}—R^{410}$ respectively to the compound I-a or a salt thereof, and a subsequent conversion of the product into a pharmaceutically acceptable salt thereof, if desired;

The order of introduction as to $—R^{45}$, $—R^{41}$ and $—R^{44}—R^{410}$ is not necessarily specified.

The compound I may also be prepared by introducing $—R^{45}$ to the compound I-a or a salt thereof, and then introducing $—R^{41}$ and $—R^{44}—R^{410}$ respectively. In this case, the order of introduction as to $—R^{41}$ and $—R^{44}—R^{410}$ is not particularly specified.

Furthermore, the compound I may also be prepared by introducing $—R^{45}$ to the compound I-a or a salt thereof, and then introducing $—R^{41}$, and then introducing $—R^{44}—R^{410}$.

Furthermore, the compound I may also be prepared by introducing $—R^{45}$ to the compound I-a or a salt thereof, and then introducing $—R^{44}—R^{410}$, and then introducing $—R^{41}$.

When a protection/deprotection step of a functional group is necessary in the preparation of the compound I described above, a conventional method may be used appropriately. A general explanation of the protecting groups and their use is described in Greene, Protective Groups in Organic Synthesis, John Wiley and Sons, New York, 1991.

Symbols of the compound I have the same meaning as those of WO 2005/095409, provided that the definition of $R^{41}$, $R^{44}$, $R^{45}$ and $R^{410}$ are the same as $R^1$, $R^4$, $R^5$, and $R^{10}$ of WO 2005/095409, respectively.

$—R^{44}—R^{410}$, $—R^{45}$ and $—R^{41}$ can be introduced according to the methods described in WO 2005/095409, page 56, line 16-page 89, line 14.

—$R^{44}$—$R^{410}$ can be introduced by using a compound of the following formula:

$$R^{410}—R^{44}—Z^{41}$$

wherein $Z^{41}$ means a leaving group and the other symbols have the same meaning as described before.

The introduction can be carried out in a suitable solvent in the presence of a base.

Examples of the leaving group include a halogen atom including a chlorine atom, a bromine atom, and an iodine atom, and a substituted sulfonyloxy group including a methanesulfonyloxy group, a p-toluenesulfonyloxy group, and a trifluoro-methanesulfonyloxy group.

A conventional base can be used as the base, and for example, alkaline metal hydride including sodium hydride, potassium hydride; alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal hydrogencarbonate including sodium hydrogencarbonate, potassium hydrogencarbonate; amines including triethylamine, diisopropylethylamine, methylpiperidine, dimethylaniline, 1,8-diazabicyclo[5.4.0]undecene, 1,4-diazabicyclo[2.2.2]octane, 1,5-diazabicyclo[4.3.0]nonene; tetrabutylammonium iodide, pyridines including pyridine, dimethylaminopyridine can be preferably used.

Any solvent which dose not disturb the reaction can be preferably used, and examples of such a solvent include, for example, hydrocarbons including pentane, hexane; aromatic hydrocarbons including benzene, toluene, nitrobenzene; halogenated hydrocarbons including dichloromethane, chloroform; ethers including diethyl ether, tert-butylmethylether, tetrahydrofuran; amides including dimethylformamide, N-methylpyrrolidone, 1,3-dimethylimidazolidin-2-one; sulfoxides including dimethyl-sulfoxide; alcohols including methanol, ethanol; esters including ethyl acetate, butyl acetate; ketones including acetone, methyl ethyl ketone; nitrites including acetonitrile; water, or a mixed solvent thereof.

The reaction is typically carried out from under cooling to under heating, preferably from −78° C. to 200° C., more preferably from −30° C. to 100° C.

—$R^{45}$ can be introduced, for example, by using a compound of the following formula:

$$R^{45}—Z^{44}$$

wherein $Z^{44}$ means a leaving group and the other symbol has the same meaning as described before.

Examples of the leaving group include a halogen atom such as a chlorine atom, a bromine atom, and an iodine atom, and a substituted sulfonyloxy group such as a methanesulfonyloxy group, a p-toluenesulfonyloxy group, and a trifluoromethane-sulfonyloxy group.

The reaction can be carried out in a suitable solvent such as toluene, 1,4-dioxane, dimethylformamide, 1,3-dimethylimidazolidinone and the like, in the presence of a base such as diisopropylethylamine and the like, or the absence of a base, from under room temperature to under heating.

Furthermore, the reaction can be carried out by adding a palladium catalyst such as palladium acetate, tris(dibenzylideneacetone)dipalladium and a phosphine such as triphenylphosphine, tributylphosphine, 2,2'-bis(diphenylphosphino)-1,1-binaphthyl and 2-(di-tert-butylphosphino) biphenyl in the presence of a base such as sodium tert-butoxide from under room temperature to under heating, if desired.

—$R^{41}$ can be introduced by reaction of a compound $$R^{41}—Z^{45}$$

wherein $Z^{45}$ means a leaving group and the other symbol has the same meaning as described before.

The introduction can be carried out in a suitable solvent in the presence of a base.

Examples of the leaving group include a halogen atom including a chlorine atom, a bromine atom, and an iodine atom, and a substituted sulfonyloxy group including a methanesulfonyloxy group, a p-toluenesulfonyloxy group, a trifluoromethanesulfonyloxy group, and an imidazolyl group including an imidazolyl group and N-methylimidazolyl group.

A conventional base can be used as the base, and for example, alkaline metal hydride including sodium hydride, potassium hydride; alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal hydrogencarbonate including sodium hydrogencarbonate, potassium hydrogencarbonate; amines including triethylamine, diisopropylethylamine, methylpiperidine, dimethylaniline, 1,8-diazabicyclo[5.4.0]undecene, 1,4-diazabicyclo[2.2.2]octane, 1,5-diazabicyclo[4.3.0]nonene; pyridines including pyridine, dimethylaminopyridine can be preferably used.

Any solvent which dose not disturb the reaction can be preferably used, and examples of such a solvent include hydrocarbons including pentane, hexane; aromatic hydrocarbons including chlorobenzen, benzene, toluene, nitrobenzene; halogenated hydrocarbons including dichloromethane, chloroform; ethers including diethylether, tetrahydrofuran; amides including dimethylformamide, N-methylpyrrolidone, 1,3-dimethylimidazolidin-2-one; sulfoxides including dimethylsulfoxide; alcohols including methanol, ethanol; esters including ethyl acetate, butyl acetate; ketones including acetone, methyl ethyl ketone; nitriles including acetonitrile; water, or a mixed solvent thereof.

The reaction is carried out from under cooling to under heating, preferably from −78° C. to 200° C., more preferably from −30° C. to 100° C.

When —$R^{41}$ is —$COXR^{411}$, wherein X means —O— or —NH— group, —$R^{41}$ can also be, for example, introduced by reacting a carbonylating agent with 1-amino group of the tetrahydroquinoline structure to give an activated derivative, and subsequent reaction of the activated derivative with $R^{411}$—X—H.

The reaction of a carbonylating agent with 1-amino group of the tetrahydroquinoline structure can be carried out in a suitable solvent in the presence or absence of a base.

A conventional carbonylating agent such as carbonyldiimidazole, phosgene, triphosgene, 4-nitrophenyl chloroformate and the like can be used.

Any solvent which dose not disturb the reaction can be preferably used, and examples of such a solvent includes, for example, hydrocarbons including pentane, hexane; aromatic hydrocarbons including chlorobenzen, benzene, toluene, nitrobenzene; halogenated hydrocarbons including dichloromethane, chloroform; ethers including diethylether, tetrahydrofuran; amides including dimethylformamide, N-methylpyrrolidone, 1,3-dimethylimidazolidin-2-one; sulfoxides including dimethylsulfoxide; alcohols including methanol, ethanol; esters including ethyl acetate, butyl acetate; ketones including acetone, methyl ethyl ketone; nitriles including acetonitrile; water, or a mixed solvent thereof.

A conventional base can be used as the base, and for example, alkaline metal hydride including sodium hydride, potassium hydride; alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; amines including triethylamine, diisopropylethylamine, methylpiperidine, dimethylaniline, 1,8-diaza-bicyclo[5.4.0]undecene, 1,4-diazabicyclo[2.2.2]octane, 1,5-diazabicyclo[4.3.0]nonene; pyridines including pyridine, dimethylaminopyridine can be preferably used.

The reaction is carried out from under cooling to under heating, preferably from $-78°$ C. to $200°$ C., more preferably from $-30°$ C. to $100°$ C.

The subsequent reaction of the activated derivative with $R^{411}$—X—H can be carried out in the same manner as the reaction of a carbonylating agent with 1-amino group of the tetrahydroquinoline structure.

—$R^{41}$ can also be introduced, for example, by alkanoylation, alkoxycarbonylation, alkylation and the like appropriately as described in WO 2005/095409.

The compound I may be converted into a pharmaceutically acceptable salt thereof, if desired.

A procedure of forming the pharmaceutically acceptable salt thereof is easily completed by adding a salt-forming agent. The resulting salt may be obtained by filtration, or recovered by evaporating the solvent.

(6) A Process of Preparing the Compound II

The compound II, a prodrug thereof, or a pharmaceutically acceptable salt of said compound or of said prodrug may be prepared by introducing —$R^{B1}$, —COOR$^{B4}$ and —$R^{B3}$ respectively to the compound I-a or a salt thereof, and converted into a pharmaceutically acceptable salt, solvate, enantiomer, racemate, diastereomer or mixture of diastereomers thereof, if desired.

When a protection/deprotection step of a functional group is necessary in the preparation of the compound II described above, a conventional method may be used appropriately. A general explanation of the protecting groups and their use is described in Greene, Protective Groups in Organic Synthesis, John Wiley and Sons, New York, 1991.

Symbols of the compound II have the same meaning as those of WO 00/17164, provided that the definition of $R^{B1}$, $Y^B$, $W^B$, $X^B$, $Z^B$, $R^{B3}$, $Q^B$, $V^B$, $R^{B4}$, $Q^{B1}$, $V^{B1}$ and $R^{B4}$ are the same as $R^1$, Y, W, X, Z, $R^3$, Q, V, $R^4$, $Q^1$, $V^1$, $R^4$ of WO 00/17164, respectively.

—$R^{B1}$, —COOR$^{B4}$ and $R^{B3}$ can be introduced according to the methods described in WO 00/17164, page 35, line 12-page 60, line 22.

—$R^{B1}$ may be introduced by using a conventional method which is described, for example, in Richard Larock, Comprehensive Organic Transformations, VCH Publishers Inc., New York, 1989; or Jerry March, Advanced Organic Chemistry, John Wiley & Sons, New York, 1985.

More specifically, it can be introduced by reacting a suitable carbonyl chloride, sulfonyl chloride, sulfinyl chloride, isocyanate or thioisocyanate in a polar aprotic solvent (preferably dichloromethane) in the presence of a base (preferably pyridine) at about $-78°$ C. to about $100°$ C. (preferably started at $0°$ C., and then warmed up to room temperature) for 1 to 24 hours (preferably 12 hours).

—COOR$^{B4}$ can be introduced by, for example, reacting a suitable activated carbonate (chloroformate, dicarbonate, or carbonyldiimidazole and then a suitable alcohol) in a polar solvent (preferably dichloromethane) in the presence of an excess amount of a base (preferably pyridine) at about $-20°$ C. to about $40°$ C. (preferably room temperature) for 1 to 24 hours (preferably 12 hours).

—$R^{B3}$ can be introduced by, for example, reacting an activated carboxylic acid to form an amide bond, and then reducing the amide using borane in an ethereal solvent such as tetrahydrofuran.

A procedure of conversion into a prodrug thereof, or a pharmaceutically acceptable salt of said compound or of said prodrug is described in WO 00/17164

(7) A Process of Preparing the Compound III

The compound III or a pharmaceutically acceptable salt, solvate, enantiomer, racemate, diastereomer, or mixture of diastereomers thereof may be prepared by introducing —(CHR$^{C6}$)$_n$—Y$^C$—R$^{C1}$, —R$^{C4a}$ and —R$^{C4b}$ respectively to the compound I-a or a salt thereof, and converted into a pharmaceutically acceptable salt, solvate, enantiomer, racemate, diastereomer, or mixture of diastereomers thereof, if desired.

When a protection/deprotection step of a functional group is necessary in the preparation of the compound III described above, a conventional method may be used appropriately. A general explanation of the protecting groups and their use is described in Greene, Protective Groups in Organic Synthesis, John Wiley and Sons, New York, 1991.

Symbols of the compound III have the same meaning as those of WO 2006/012093, provided that the definition of $Y^C$, $R^{C1}$, $R^{C7}$, $R^{C8}$, $R^{C11}$, $R^{C12}$, $R^{C4a}$, $R^{C10}$ and $R^{C4b}$ are the same as Y, $R^1$, $R^7$, $R^8$, $R^{11}$, $R^{12}$, $R^{4a}$, $R^{10}$ and $R^{4b}$ of WO 2006/012093 respectively.

—(CHR$^{C6}$)$_n$—Y$^C$—R$^{C1}$, —R$^{C4a}$ and —R$^{C4b}$ can be introduced according to the methods described in WO 2006/012093, page 22, line 1-page 35, line 5.

—(CHR$^{C6}$)$_n$—Y$^C$—R$^{C1}$ can be introduced by, for example, reacting optionally substituted arylchloroformate or optionally substituted alkylchloroformate in the presence of a organic base such as pyridine and the like.

—R$^{C4a}$ can be introduced by, for example, reacting an activated heteroaryl substrate such as mesylate, tosylate, bromide and the like in the presence of a base.

As to the base for example, alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; alkali metal phosphate including potassium phosphate; amines including triethylamine, diisopropylethylamine, methylpiperidine, dicyclohexylamine; pyridines including pyridine, 4-dimethylaminopyridine can be preferably used.

—R$^{C4b}$ can be introduced by, for example, reacting the amino group with benzaldehyde to give a Schiff base, and then reducing the base using a reducing reagent such as sodium borohydride and the like in a suitable solvent such as tetrahydrofuran, methanol and the like.

A procedure of conversion into a pharmaceutically acceptable salt, solvate, enantiomer, racemate, diastereomer, or mixture of diastereomers thereof is described in WO 2006/012093.

(8) A Process of Preparing the Compound I-h

The compound I-h may be prepared by an asymmetric cyclization of propylidene-(4-trifluoromethyl-phenyl)-amine or an equivalent thereof with an optionally protected vinyl amine of the formula I-g in a suitable solvent in the presence of an optically active acid catalyst.

Any solvent which dose not disturb the reaction can be preferably used, and examples of such a solvent include water; ethers including diethyl ether, tetrahydro-furan (THF), dioxane, 1,2-dimethoxyethane, diglyme; hydrocarbons including benzene, toluene, hexane, xylene; haloalkanes including dichloromethane, chloroform, 1,2-dichloroethane; alcohols including methanol, ethanol, isopropyl alcohol, tert-butanol; esters including ethyl acetate, methyl acetate, butyl acetate; polar solvents including acetone, N,N-dimethylformamide, dimethylsulfoxide and the like, or a mixture thereof. In the present reaction, dichloromethane, tetrahydrofuran (THF), dioxane, toluene, N,N-dimethylformamide and dimethylsulfoxide are preferred.

In general, the reaction temperature may be adjusted in a range of −100° C. to 100° C., preferably −100° C. to room temperature. Lower temperature is desirable in order to achieve high stereoselectivily.

Examples of the equivalent of propylidene-(4-trifluoromethyl-phenyl)-amine include (1-benzotriazol-1-yl-propyl)-(4-trifluoromethyl-phenyl)-amine.

Examples of the optically active acid catalyst include an optically active Lewis acid catalyst and an optically active Brönsted acid catalyst.

Any species having a good catalyst activity and stereoselectivity may be used as the optically active Brönsted acid catalyst, and examples of the said catalyst include TADDOL, (R)- or (S)-1,1'-binaphthyl-2,2'-diyl hydrogen phosphate, and camphorsulfonic acid.

TADDOL is a general term of a compound shown in the formula below:

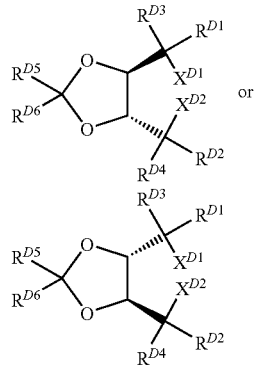

wherein $X^{D1}$ and $X^{D2}$ are a hydroxyl group; $R^{D1}$, $R^{D2}$, $R^{D3}$, and $R^{D4}$ are the same or different, an aryl group optionally substituted with one or two group(s) selected independently from a halogen atom, a nitro group, an alkoxy group, an aryl group, an aryloxy group and an alkyl group optionally substituted with halogen atom(s); $R^{D5}$ and $R^{D6}$ are the same or different, a group selected independently from an alkyl group, a phenyl group and a naphthyl group; and $R^{D5}$ and $R^{D6}$ may be substituted with one or more group(s) selected from an alkyl group optionally substituted with a halogen atom, a halogen atom, a nitro group, an alkoxy group, an aryl group and an aryloxy group.

Among the optically active Brönsted acid catalyst, (R)- or (S)-1,1'-binaphthyl-2,2'-diyl hydrogen phosphate, camphorsulfonic acid and TADDOL wherein $R^{D5}$ and $R^{D6}$ are methyl groups, $X^{D1}$ and $X^{D2}$ are hydroxyl groups, and $R^{D1}$, $R^{D2}$, $R^{D3}$ and $R^{D4}$ are naphthyl groups are preferable.

Examples of the optically active Lewis acid catalyst include a compound comprising an optically active ligand and a Lewis acidic atom.

A Lewis acidic atom includes, for example, boron, aluminum, titanium, zirconium, zinc, magnesium, ytterbium, scandium, samarium, copper, silver, iron, palladium and the like. Among them, boron, aluminum, titanium, zirconium, ytterbium, scandium, copper and palladium are preferable. Boron, aluminum, titanium and ytterbium are more preferable. Boron is especially preferable.

Any species having a good catalyst activity and stereoselectivity may be used as the optically active ligand, and examples of the ligand include a biphenol derivative, a 1,1'-binaphthol derivative, an 1,1'-octahydrobinaphthol derivative, an 1,2-ethanediol derivative, an ethylenediamine derivative, a tartrate derivative, a bisbinaphthol derivative, TADDOL, a prolinol derivative, an α-amino acid derivative, a 2,2'-bisoxazolinyl propane derivative, a BINAP derivative.

Any optionally substituted 1,1-binaphthol may be used as the 1,1-binaphthol derivative. Preferably, a compound of the general formula shown below:

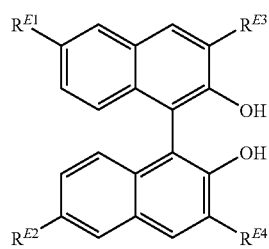

wherein $R^{E1}$ and $R^{E2}$ are the same or different, a hydrogen atom, a halogen atom, an alkyl group optionally substituted with one to six halogen atom(s), an alkoxy group optionally substituted with one to six halogen atom(s); $R^{E3}$ and $R^{E4}$ are, the same or different, a hydrogen atom, a halogen atom, an alkyl group optionally substituted with one to six halogen atom(s), an alkoxy group optionally substituted with one to six halogen atom(s), a phenyl group optionally substituted with one to five group(s) selected independently from an alkyl group, an alkyl group substituted with one to six halogen atom(s), and a hydroxyl group, may be used as a 1,1'-binaphthol derivative. More preferably, (R)-1,1'-binaphthol, (R)-3,3'-dibromo-1,1'-bi-2-naphthol and (R)-6,6'-dibromo-1,1'-bi-2-naphthol may be used.

Any optionally substituted 1,1-octahydrobinaphthol may be used as the 1,1'-octahydrobinaphthol derivative. Preferably, a compound of the general formula shown below:

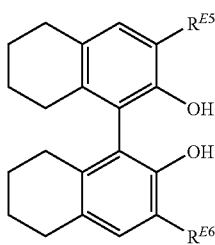

wherein $R^{E5}$ and $R^{E6}$ are the same or different, a hydrogen atom, a halogen atom, an alkyl group optionally substituted with one to six halogen atom(s), an alkoxy group optionally substituted with one to six halogen atom(s), a phenyl group optionally substituted with one to five group(s) selected independently from an alkyl group, a hydroxyl group and an alkyl group substituted with one to six halogen atom(s) may be used as the 1,1'-octahydrobinaphthol derivative. More preferably, (R)-5,5',6,6',7,7',8,8'-octahydro-bi-2-naphthol may be used.

Any optionally substituted biphenol may be used as the biphenol derivative. Preferably, a compound of the general formula shown below:

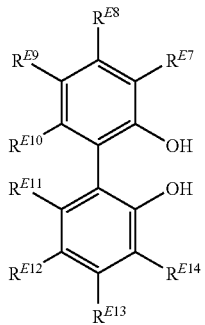

wherein $R^{E8}$, $R^{E9}$, $R^{E10}$, $R^{E11}$, $R^{E12}$ and $R^{E13}$ are the same or different, a hydrogen atom, a halogen atom, an alkyl group optionally substituted with one to six halogen atom(s), an alkoxy group optionally substituted with one to six halogen atom(s); $R^{E7}$ and $R^{E14}$ are the same or different, a hydrogen atom, a halogen atom, an alkyl group optionally substituted with one to six halogen atom(s), an alkoxy group optionally substituted with one to six halogen atom(s), a phenyl group optionally substituted with one to five group(s) selected independently from an alkyl group, a hydroxyl group and an alkyl group substituted with one to six halogen atom(s) may be used as the biphenol derivative. More preferably, (R)- or (S)-5,5',6,6'-tetramethyl-3,3'-di-tert-butyl-1,1'-biphenyl-2,2'-diol may be used as the biphenol derivative. Especially preferably, (R)-5,5',6,6'-tetramethyl-3,3'-di-tert-butyl-1,1'-biphenyl-2,2'-diol may be used as the biphenol derivative.

Any optionally substituted 1,2-ethanediol may be used as the 1,2-ethanediol derivative. Preferably, (R,R)- or (S,S)-1,2-diphenyl-1,2-ethanediol may be used as the 1,2-ethandiol derivative.

Any optionally substituted ethylenediamine may be used as the ethylenediamine derivative. Preferably, (1R,2R)- or (1S,2S)-1,2-diphenylethylenediamine may be used as the ethylenediamine derivative.

Any optionally substituted tartrate may be used as the tartrate derivative. Preferably, diisopropyl D- or L-tartrate may be used as the tartrate derivative.

A bisnaphthol derivative includes, for example, 3,3"-[oxy-bis(methylene)]bis-(1R,1"R)-1,1'-bi-2-naphthol.

Any optionally substituted prolinol may be used as the prolinol derivative. Preferably, (R)- or (S)-2-(diphenylhydroxymethyl)pyrrolidine may be used as the prolinol derivative.

Any optionally substituted α-amino acid may be used as the α-amino acid derivative. Preferably, (R)- or (S)-3-(1H-indol-3-yl)-2-(toluene-4-sulfonylamino)-propionic acid may be used as the α-amino acid derivative.

Any optionally substituted 2,2'-bisoxazolinyl propane may be used as the 2,2'-bisoxazolinyl propane derivative. Preferably, (R,R)- or (S,S)-2,2'-bis(4-tert-butyl-2-oxazolin-2-yl) propane, (R,R)- or (S,S)-2,2'-bis(4-phenyl-2-oxazolin-2-yl) propane may be used as the 2,2'-bisoxazolinyl propane derivative.

Any optionally substituted BINAP may be used as the BINAP derivative. Preferably, (R)- or (S)-2,2'-bis(diphenylphosphino)-1,1'-binaphthyl may be used as the BINAP derivative.

A hydroxyl group, an amino group and a sulfonylamino group of the above listed optically active ligand can be coordinated with the above listed Lewis acidic atom as a hydroxy anion, an amino anion, and a sulfonylamino anion respectively.

The above listed optically active ligand can be coordinated with the above listed Lewis acidic atom in the ratio except for 1:1.

The optically active Lewis acid catalyst can include a compound comprising an optically active ligand, a Lewis acidic atom and a counter anion.

Examples of the counter anion include a halogen anion, an alkoxy anion, a phenoxy anion, an acetate anion, a trifluoroacetate anion, a triflate anion, an alkyl anion, a tolyl anion, a perchlorate anion and the like. Among them, a halogen anion, an alkoxy anion, a phenoxy anion, a triflate anion, an alkyl anion and a tolyl anion are preferable. A halogen anion, an alkoxy anion, a phenoxy anion and a triflate anion are more preferable.

The amount of the optically active acid catalyst is 0.01 to 1 equivalent, preferably 0.05 to 0.5 equivalent per 1 equivalent of the substrate.

The amino-protecting group in an optionally protected vinyl amine of the compound I-g, may be selected from protecting groups which are conventionally used for protection of an amino group, and such protecting groups are described in Greene, Protective Groups in Organic Synthesis, John Wiley and Sons, New York, 1991. Preferably, a carbamate protecting group such as a tert-butoxycarbonyl group, a benzyloxycarbonyl group, a 9-fluorenylmethyloxycarbonyl group, a 2,2,2-trichloro-ethoxycarbonyl group, an allyloxycarbonyl group, a 1-naphthalenemethoxycarbonyl group, a 2-naphthalenemethoxycarbonyl group and the like; an amide protecting group such as a trifluoroacetyl group and the like; an imide protecting group such as a phthaloyl group and the like; and a sulfonamide protecting group such as a p-toluenesulfonyl group, a nitrobenzenesulfonyl group and the like are used. More preferably, a benzyloxycarbonyl group, a tert-butoxycarbonyl group, a 1-naphthalenemethoxycarbonyl group, a 2-naphthalenemethoxycarbonyl group and a phthaloyl group are used.

The deprotection step in the preparation of the compound I-a from the compound I-h, can be carried out by a conventional method described in Greene, Protective Groups in Organic Synthesis, John Wiley and Sons, New York, 1991 can be used.

A procedure of forming a salt is easily completed by adding a salt-forming agent according to (4) described above. The resulting salt may be obtained by filtration, or recovered by evaporating the solvent.

EFFECT OF THE INVENTION

The present invention is useful for efficient preparation of optically active tetrahydroquinoline derivatives which have CETP inhibitory activity, and show effects of increasing HDL cholesterol level and decreasing LDL cholesterol level, and for preparation of a synthetic intermediate thereof.

According to the process of the present invention, the optically active tetrahydroquinoline derivatives and the synthetic intermediate compound I-a can be efficiently prepared with fewer steps and without an optical resolution and/or protection/deprotection of the functional groups.

Moreover, (R)-3-(4-trifluoromethyl-phenylamino)-valeric acid with no bulky substituent on it can be stereoselectively cyclized according to the process of the present invention.

Furthermore, (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime can be stereoselectively reduced to give the desired compound I-a according to the process of the present invention.

Furthermore, stereoselective cyclization of propylidene-(4-trifluoromethyl-phenyl)-amine or its equivalent with an optionally protected vinyl amine can be proceeded in the presence of an optically active acid catalyst.

BEST MODE FOR CARRYING OUT THE INVENTION

The process for preparing the compounds of the present invention is illustrated in more detail by Examples and Reference Examples but the present invention should not be construed to be limited thereto.

Example 1

(1) (R)-3-(4-Trifluoromethyl-phenylamino)-valeric acid

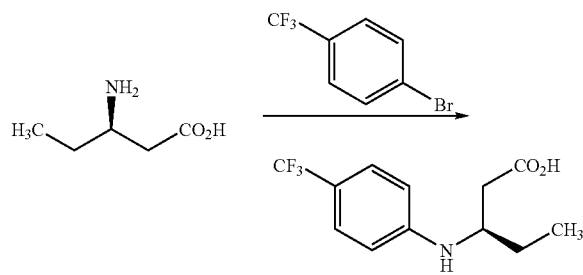

To a solution of 1-bromo-4-trifluoromethylbenzene (2530 g, 11.24 mole) and (R)-3-aminovaleric acid (659 g, 5.63 mole) in N,N-dimethylformamide (12 liter), were added copper iodide (210 g, 1.10 mole) and potassium carbonate (2330 g, 16.86 mole), and the mixture was sealed under nitrogen atmosphere and stirred at 100° C.-120° C. for about 60 hours. When the reaction was completed, the reaction mixture was concentrated in vacuo at 60° C.-70° C. of the bath temperature, the residue was dissolved in water (6.0 liter) and the solution was adjusted to pH about 5.0 with addition of hydrochloric acid. Ethyl acetate (6.0 liter) was added and the mixture was stirred, filtered and washed with ethyl acetate (2.4 liter). The filtrate was separated and the aqueous layer was extracted with ethyl acetate (3.6 liter). The organic layer was combined and extracted with 25% ammonia water (3.0 liter) and water (3 liter). The aqueous layer was acidified to pH about 5.0 with addition of hydrochloric acid, and extracted with ethyl acetate (6.0 liter). The organic layer was dried over magnesium sulfate (600 g), filtered and washed with ethyl acetate (2.4 liter). The filtrate was concentrated in vacuo at 45° C.-55° C. of the bath temperature, and the titled compound was obtained as an oily residue, which was used in the next step without further purification.

(2) (R)-2-Ethyl-6-trifluoromethyl-2,3-dihydro-1H-quinolin-4-one

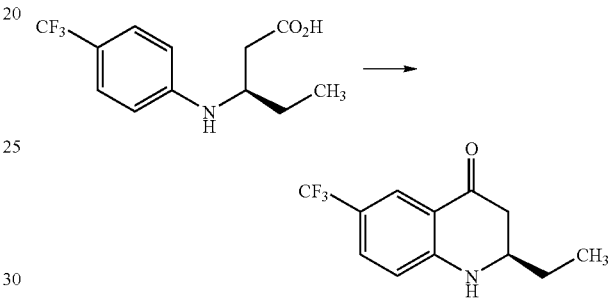

Phosphorus pentoxide (600 g) was dissolved in methanesulfonic acid (6.0 liter) at below 40° C., the solution was added to the compound (1200 g) obtained in Example 1 (1) above and the mixture was stirred under nitrogen atmosphere at 65-75° C. for 3-4 hours. When the reaction was completed, the reaction mixture was cooled, 12N sodium hydroxide aqueous solution was added dropwise thereto at below 40° C. and the mixture was adjusted to pH 10-12. Ethyl acetate (6.0 liter) was added and the mixture was stirred, filtered and washed with ethyl acetate (6.0 liter). The filtrate was separated and the organic layer was washed with 25% ammonia water (1.8 liter) and water (1.8 liter). The organic layer was further washed with water (3.6 liter) and concentrated in vacuo at 45-55° C. of the bath temperature. The residue was dissolved in ethyl acetate (1.2 liter) and n-hexane (4.8 liter) at 50-70° C. and n-hexane (4.8 liter) was added dropwise at the same temperature. After cooled to below 10° C., the mixture was filtered and the crystalline was washed with chilled ethyl acetate/n-hexane=1/20 (1.2 liter). The wet product was air-dried or dried under reduced pressure at 45-55° C. and the titled compound was obtained (496 g, yield 44%).

(3) (R)-2-Ethyl-6-trifluoromethyl-2,3-dihydro-1H-quinolin-4-one oxime

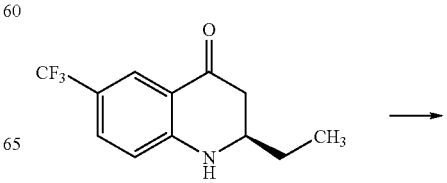

-continued

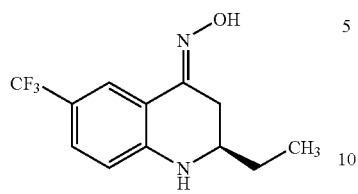

The compound obtained in the Example 1 (2) above (470 g), hydroxylamine hydrochloride (671 g) and ethanol (7.1 liter) were added in this order to a reaction vessel and suspended. Pyridine (1.4 liter) was added and the mixture was heated to reflux for 2 hours. When the reaction was completed, the mixture was cooled to about 25° C. and the solvent was evaporated. To the residue, dichloromethane (14.5 liter) and 1N hydrochloric acid (7.1 liter) was added and the mixture was separated. The aqueous layer was confirmed to be pH about 1 using a pH-test paper. The aqueous layer was separated, a saturated aqueous sodium hydrogen carbonate solution (7.1 liter) was added and separated. The pH of the aqueous layer was confirmed to be over 8 using a pH-test paper. The aqueous layer was separated and the organic layer was dried over magnesium sulfate (94 g). After filtration, the filtrate was concentrated and the titled compound was obtained as a crystalline (1.32 g, yield 96%).

(4) (2R,4S)-2-Ethyl-6-trifluoromethyl-1,2,3,4-tetrahydroquinolin-4-ylamine methanesulfonate

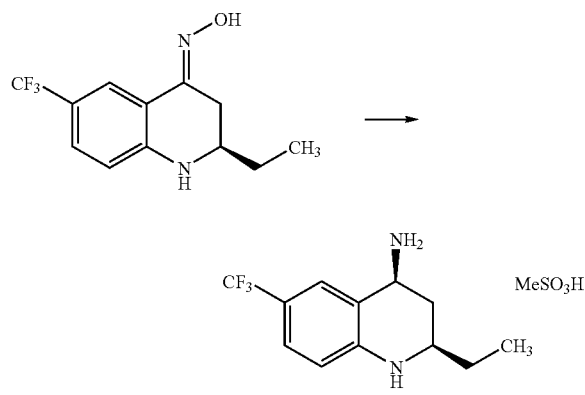

The compound obtained in Example 1 (3) above (380 g) was dissolved in ethanol (2.85 liter) in an autoclave, and 10% palladium carbon (167 g) was added. After replacement with nitrogen gas, the gas was replaced with hydrogen gas three times and the reaction was carried out under 5 atoms at 40° C. for 16 hours. After the reaction was completed, the mixture was filtered, the insoluble materials were washed with ethanol (1.0 liter) twice and the filtrate was concentrated. The residue was dissolved in isopropyl alcohol (1.9 liter), and to the solution was added methanesulfonic acid (141 g) at room temperature and stirred. After precipitation, n-heptane (5.7 liter) was added and the stirring was continued at room temperature for 3 hours. The precipitated crystalline was collected by filtration, washed with n-heptane (1.1 liter), dried in vacuo at about 40° C. to give the titled methanesulfonate (375 g, yield 75%).

Example 2

(1) (R)-3-(4-Trifluoromethyl-phenylamino)-valeric acid

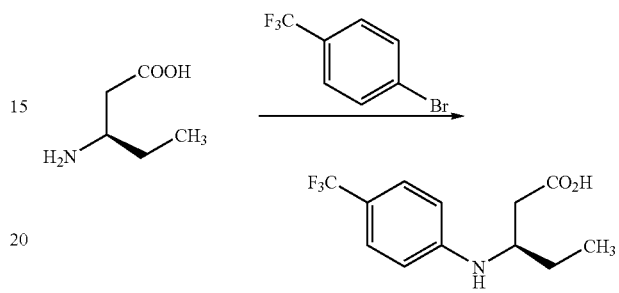

(R)-3-Aminovaleric acid (12 kg), 1-bromo-4-trifluoromethylbenzene (34.6 kg), copper iodide (3.9 kg) and potassium carbonate (28.3 kg) were added to dimethylsulfoxide (120 liter), and the mixture was sealed under nitrogen atmosphere and stirred at 100-120° C. for 48 hours. After the reaction mixture was cooled, water (120 liter) and toluene (120 liter) were added, the value of the pH was adjusted to below 3 with addition of hydrochloric acid and the solution was separated. The aqueous layer was extracted with toluene (120 liter) and the combined organic layer was washed with water (120 liter). 25% ammonia water (60 liter) and water (60 liter) were added to the organic layer and extracted. The aqueous layer was adjusted to pH 3-4 with addition of hydrochloric acid and extracted with toluene (120 liter). The filtrate was concentrated in vacuo at 30-70° C. of the bath temperature, n-heptane (24 liter) was added to the residue and concentrated twice to give the titled compound as an oily residue. The product was used in the next step without further purification. MS (APCI) m/z: 262 [M+H]$^+$.

(2) (R)-2-Ethyl-6-trifluoromethyl-2,3-dihydro-1H-quinolin-4-one

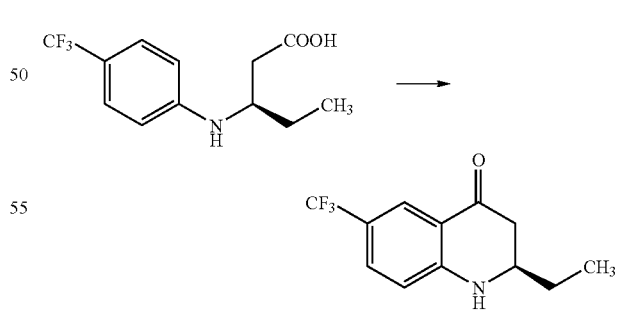

Phosphorus pentoxide (13.1 kg) was dissolved in methanesulfonic acid (131 liter) warmed, the solution was added to the compound (26.27 kg) obtained in Example 2 (1) above and the mixture was stirred at 65-75° C. for about 3 hours. To the reaction mixture, was added water (342 liter) dropwise while keeping the temperature at 10-50° C., and then the solution was cooled at below 10° C. The precipitated crystalline was collected by filtration and washed with water (393 liter). When the pH of the washing was acidic, the precipitate was washed again. The wet crystalline was dissolved in ethyl acetate (26.3 liter) and n-heptane (105 liter) at 60-70° C., and n-heptane (158 liter) was further added at the same temperature. The solution was stirred at 45-50 for about 3 hours, cooled to below 10° C., and the precipitated crystalline was filtered and washed with ethyl acetate/n-heptane=1/10 (26.3 liter). The wet product was dried under reduced pressure at below 50° C. to give the titled compound (11.5 kg, yield 47%). MS (APCI) m/z: 244 [M+H]+.

(3) (R)-2-Ethyl-6-trifluoromethyl-2,3-dihydro-1H-quinolin-4-one oxime

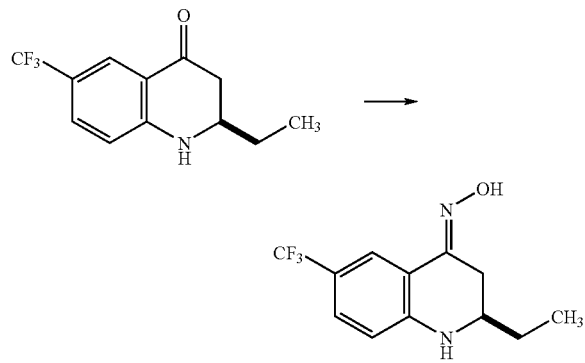

The compound obtained in the Example 2 (2) (11.1 kg), hydroxylamine sulfate (5.62 kg), sodium acetate (7.49 kg) and water (11.1 liter) was mixed with tetrahydrofuran (111 liter) and stirred at 45-50° C. for about 11 hours. After the mixture was cooled, toluene (111 liter) and water (55.5 liter) were added thereto and extracted, a saturated aqueous sodium hydrogen carbonate solution (55.5 liter) was added to the organic layer and the solution was separated. The organic layer was washed with water (55.5 liter), and then brine (55.5 liter). The organic layer was concentrated in vacuo, toluene (22.2 liter) was added to the residue and concentrated twice, and then n-heptane (111 liter) was added at 50-60° C. After the mixture was cooled to 25-30° C., the precipitate was collected by filtration and the crystalline was washed with n-heptane (22.2 liter). The wet product was dried under reduced pressure at below 30° C. and the titled compound was obtained (9.86 kg, yield 84%). MS (APCI) m/z: 259 [M+H]+.

(4) (2R,4S)-2-Ethyl-6-trifluoromethyl-1,2,3,4-tetrahydroquinolin-4-ylamine methanesulfonate

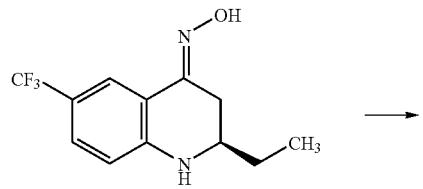

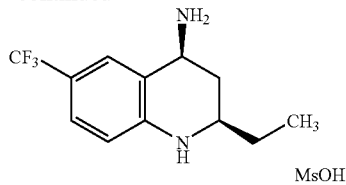

In a pressure vessel, the compound obtained in Example 2 (3) (9.4 kg) was dissolved in isopropyl alcohol (47 liter) and 10% palladium carbon (including water 57%, 2.63 kg) was added. After replacement with nitrogen gas, the gas was replaced with hydrogen gas three times and the reaction was carried out under 5 atoms at about 40° C. for 8 hours. The reaction mixture was cooled, the palladium carbon was filtered off and washed with isopropyl alcohol (18.8 liter). The filtrate was concentrated, n-heptane (47 liter) was added to the residue and thereto was added methanesulfonic acid (3.5 kg) dissolved in isopropyl alcohol (9.4 liter). When precipitation of a crystalline was observed, n-heptane (94 liter) was added and the mixture was stirred at 20-30° C. for about 3 hours. The crystalline was collected by filtration, and washed with n-heptane (16.5 liter) and isopropyl alcohol (2.3 liter). The wet product was dried under reduced pressure at about 40° C. to give the titled compound as a crystalline (9.45 kg, yield 75%). MS (APCI) m/z: 245 [M+H]+, 228 [M−NH2].

Example 3

(1) (R)-3-(4-Trifluoromethyl-phenylamino)-valeric acid

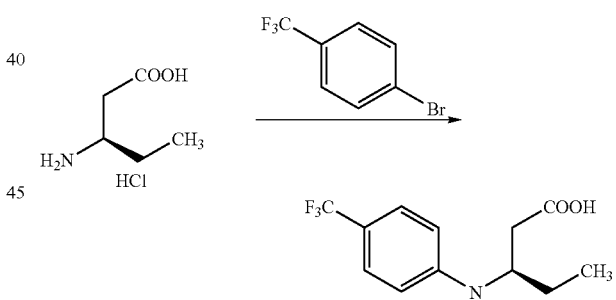

To (R)-3-aminovaleric acid hydrochloride (5.0 g), were added 1-bromo-4-trifluoromethylbenzene (10.95 g), copper iodide (1.24 g), potassium carbonate (13.5 g) and dimethylsulfoxide (50 ml), the mixture was stirred under nitrogen atmosphere in a sealed vessel at about 110° C. for 46 hours. The reaction mixture was cooled, water (50 ml) and toluene (50 ml) was added thereto, the pH was adjusted to 3-4 with addition of hydrochloric acid (12.5 mL) and the solution was separated. The aqueous layer was extracted with toluene (50 ml) and the combined organic layer was washed with water (50 ml). 28% ammonia water (50 ml) and water (50 ml) were added to the organic layer and the product was extracted with the aqueous layer. To the aqueous layer were added toluene (50 ml) and hydrochloric acid (30 ml) and the solution was separated. The organic layer was concentrated in vacuo at about 60° C. of the bath temperature, n-heptane (16.3 g) was added to the residue and evaporated twice to give the titled compound as an oily residue. The product was used in the next step without purification.

(2) (R)-2-Ethyl-6-trifluoromethyl-2,3-dihydro-1H-quinolin-4-one

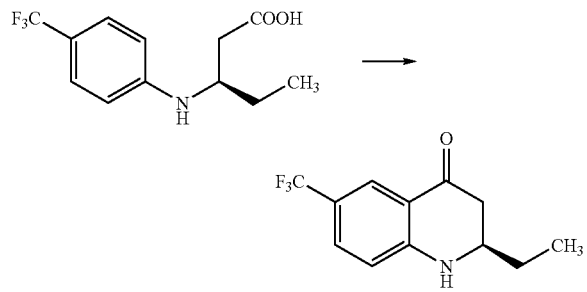

Phosphorus pentoxide (4.24 g) was dissolved in methanesulfonic acid (42.35 ml) warmed, the solution was added to the compound (8.47 g) obtained in Example 3 (1) above and the mixture was stirred at about 70° C. for 5 hours. The reaction mixture was cooled to about 10° C. and water (110 ml) was added dropwise while keeping the temperature at 10-50° C. with cooling. The mixture was cooled to below 10° C. after water was added. The crystalline was isolated by centrifugation, washed with water (127 ml), and the wet product was dissolved in ethyl acetate (8.5 ml) and n-heptane (34 ml) at 60-70° C. and thereto was added n-heptane (51 ml). After cooled to 5-10° C., the crystalline was filtered off and washed with chilled ethyl acetate/n-heptane=1/10 (9.3 ml). The wet product was dried under reduced pressure at about 50° C. of the bath temperature to give the titled compound (4.75 g, yield from step (1) 60.2%).

Example 4

(1) (2R,4S)-2-Ethyl-6-trifluoromethyl-1,2,3,4-tetrahydroquinolin-4-ylamine

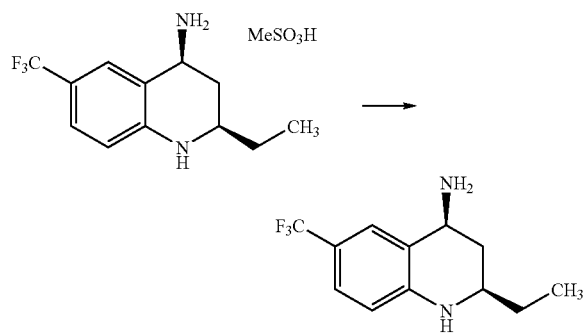

Water (0.1 ml) and sodium tert-butoxide (212 mg) were added to a solution of (2R,4S)-2-ethyl-6-trifluoromethyl-1,2,3,4-tetrahydroquinolin-4-ylamine methane-sulfonate (500 mg) in toluene (2.5 ml) and the mixture was stirred at 80° C. for an hour. Thereto was added water (2.5 ml) and the mixture was stirred at 80° C. for 1.5 hours. The reaction mixture was cooled to room temperature and the organic layer was separated, washed with a saturated brine, dried over magnesium sulfate and concentrated in vacuo to give the titled compound.

(2) (2R,4S)-4-[5-(4-Tert-butoxycarbonylbutoxy)pyrimidin-2-yl-amino]-2-ethyl-6-trifluoromethyl-1,2,3,4-tetrahydroquinoline

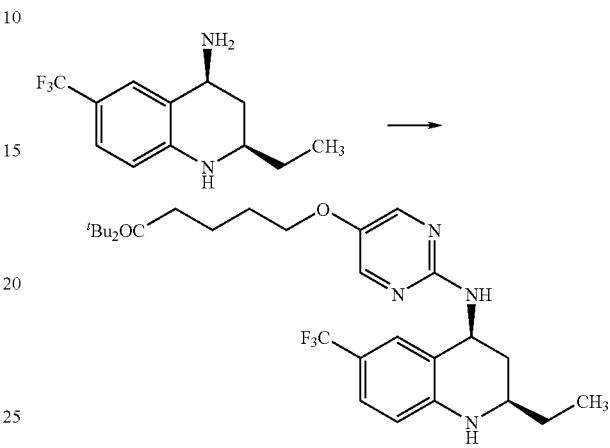

5-(2-Chloropyrimidine-5-yloxy)-pentanoic acid tert-butyl ester (464 mg), palladium acetate (26 mg), 2,2'-bis(diphenylphosphino)-1,1'-binaphthyl (81 mg) were dissolved in toluene (0.5 ml) and the mixture was stirred under nitrogen atmosphere at 50° C. for an hour. The reaction mixture was cooled to room temperature, thereto was added the compound obtained in Example 4 (1) dissolved in toluene (9.5 ml) and stirred at room temperature for 15 minutes. Then, sodium tert-butoxide (310 mg) was added and the mixture was stirred at room temperature for 4 days. Water and ethyl acetate was added to the mixture and the organic layer was separated, washed with a saturated brine, dried over magnesium sulfate and concentrated in vacuo. The resulting residue was purified by column chromatography (silica gel; hexane:ethyl acetate=49:1→17:3→4:1) to give the titled compound (537 mg). MS (m/z): 495 [M+H]⁺.

Example 5

(2R,4S)-4-[5-(4-Tert-butoxycarbonylbutoxy)pyrimidin-2-ylamino]-2-ethyl-6-trifluoro-methyl-3,4-dihydro-2H-quinoline-1-carboxylic acid ethyl ester

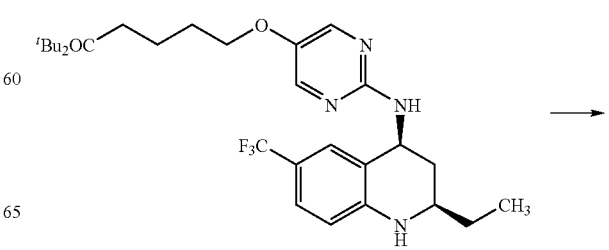

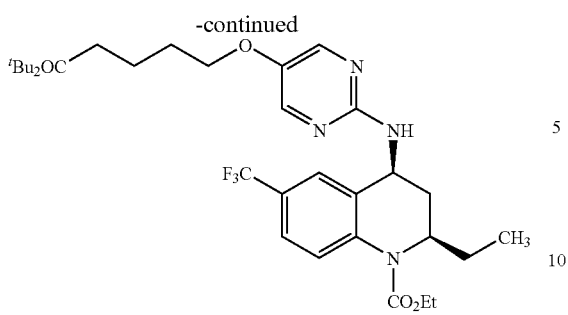

Ethyl chloroformate (510 µl) was added to a solution of the compound obtained in Example 4 (2) (527 mg) in chlorobenzene (3.7 ml) under nitrogen atmosphere at 10° C. and pyridine (430 µl) was added to the mixture at below 30° C. After being stirred at room temperature for a day, ethyl chloroformate (315 µl) and pyridine (258 µl) were added and the mixture was further stirred at room temperature for 2.5 hours. Water and ethyl acetate were added to the mixture and the organic layer was separated, washed with 1N hydrochloric acid and a saturated brine, dried over magnesium sulfate and concentrated in vacuo. The resulting residue was purified by column chromatography (silica gel; hexane:ethyl acetate=49:1→4:1) to give the titled compound (228 mg). MS (m/z): 567[M+H]⁺.

Example 6

(2R,4S)-4-{(3.5-Bis-(trifluoromethylbenzyl)-[5-(4-tert-butoxycarbonylbutoxy)-pyrimidin-2-yl]amino}-2-ethyl-6-trifluoromethyl-3,4-dihydro-2H-quinoline-1-carboxylic acid ethyl ester

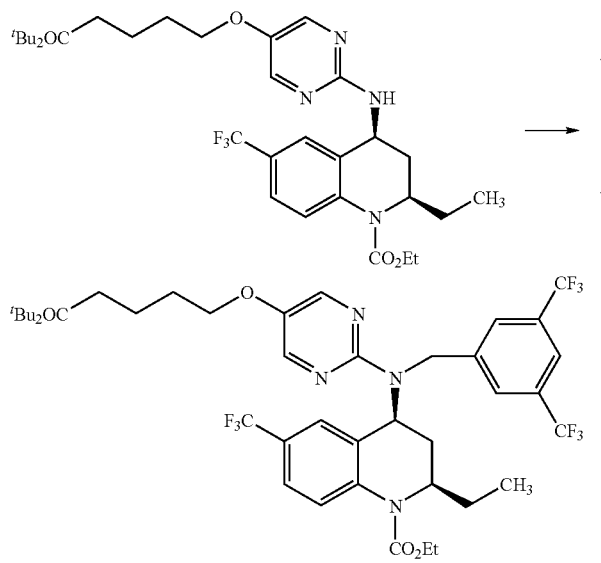

Tetrabutylammonium iodide (30 mg) and potassium tert-butoxide (135 mg) were added to a solution of the compound obtained in Example 5 (228 mg) in tert-butyl methyl ether (3.4 ml) under nitrogen atmosphere at −10° C., and then 3,5-bis(trifluoro-methyl)benzyl bromide (184 mg) dissolved in tert-butyl methyl ether (1.1 ml) was added at −10° C. to −5° C. of the inner temperature, and the mixture was stirred at −10° C. for 2 hours. Thereto were added 1N HCl and ethyl acetate, the organic layer was separated, washed with a saturated brine, dried over magnesium sulfate and concentrated in vacuo. The resulting residue was purified by column chromatography (silica gel; hexane:ethyl acetate=49:1→17:3) to give the titled compound (255 mg). MS (m/z): 793 [M+H]⁺.

Example 7

(2R,4S)-4-{(3.5-Bis-(trifluoromethylbenzyl)-[5-(4-carboxybutoxy)pyrimidin-2-yl]-amino}-2-ethyl-6-trifluoromethyl-3,4-dihydro-2H-quinoline-1-carboxylic acid ethyl ester

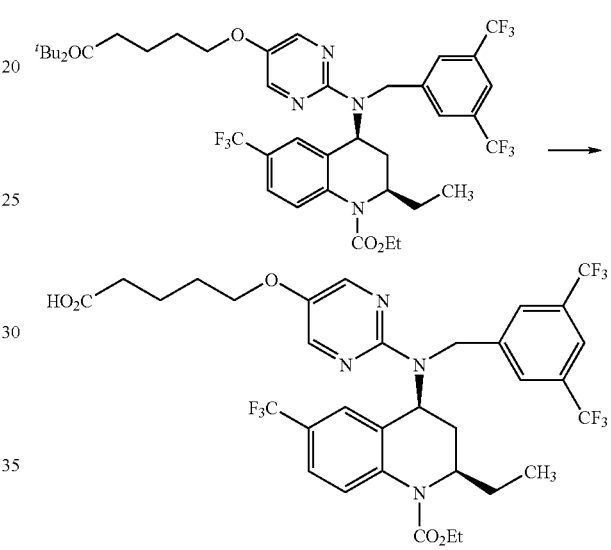

5N HCl (0.5 ml) was added to a solution of the compound obtained in Example 6 (250 mg) in acetic acid (1.5 ml) and the mixture was stirred at 50° C. for 3 hours. The reaction mixture was cooled to room temperature, water and ethyl acetate was added to the mixture and the organic layer was separated, washed with a saturated aqueous sodium hydrogen carbonate solution three times and then with a saturated brine, dried over magnesium sulfate and concentrated in vacuo. The resulting residue was purified by column chromatography (silica gel; hexane:ethyl acetate=4:1→1:1) to give the titled compound (183 mg). MS (m/z): 737 [M+H]⁺.

Example 8

(1) (2R,4S)-2-Ethyl-6-trifluoromethyl-1,2,3,4-tetrahydroquinolin-4-ylamine

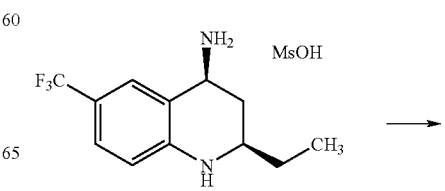

-continued

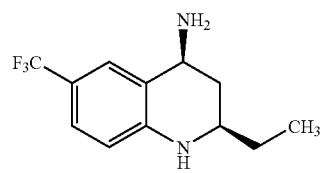

Water (0.6 ml) and sodium tert-butoxide (1.27 g) were added to a solution of (2R,4S)-2-ethyl-6-trifluoromethyl-1,2,3,4-tetrahydroquinolin-4-ylamine methane-sulfonate (3 g) in toluene (15 ml) and the mixture was stirred at 80° C. for an hour, then water (15 ml) was added, and the mixture was further stirred at 80° C. for an hour. The reaction mixture was cooled to room temperature, and the organic layer was separated, washed with a saturated brine, dried over magnesium sulfate and concentrated in vacuo to give the titled compound.

(2) (2R,4S)-4-(5-Morpholin-4-yl-pyridin-2-yl-amino)-2-ethyl-6-trifluoromethyl-1,2,3,4-tetrahydroquinoline

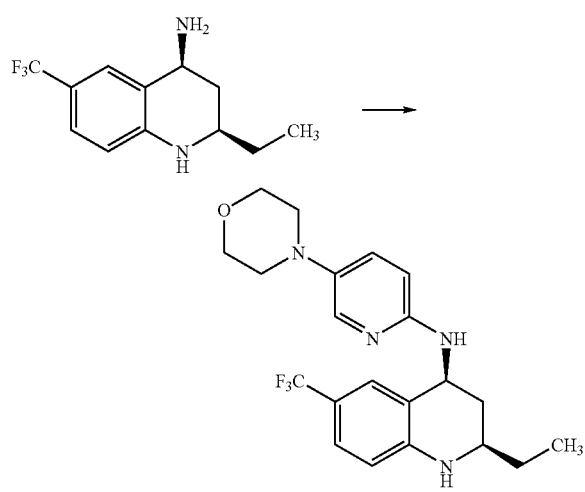

4-(6-Bromo-pyridin-3-yl)-morpholine (3.16 g), tris(dibenzylideneacetone)-dipalladium (806 mg), and 2,2'-bis(diphenylphosphino)-1,1'-binaphthyl (2.2 g) were dissolved in toluene (60 ml) and the mixture was stirred under nitrogen atmosphere at 50° C. for an hour. The reaction mixture was cooled to room temperature, thereto was added the compound obtained in Example 8 (1) dissolved in toluene (10 ml) and the mixture was stirred at room temperature for 15 minutes. The stirring was further continued at 50° C. overnight after addition of sodium tert-butoxide (1.86 g). Water and ethyl acetate were added to the reaction mixture, and the organic layer was separated, washed with a saturated brine, dried over magnesium sulfate and concentrated in vacuo to give the titled compound. The resulting residue was purified by column chromatography (silica gel; hexane:ethyl acetate=4:1→3:2) to give the titled compound (1.1 g). MS (m/z): 407 [M+H]$^+$.

Example 9

(1) (2R,4S)-2-Ethyl-4-(5-morpholin-4-yl-pyridin-2-ylamino)-6-trifluoromethyl-3,4-dihydro-2H-quinoline-1-carboxylic acid 4-nitrophenyl ester

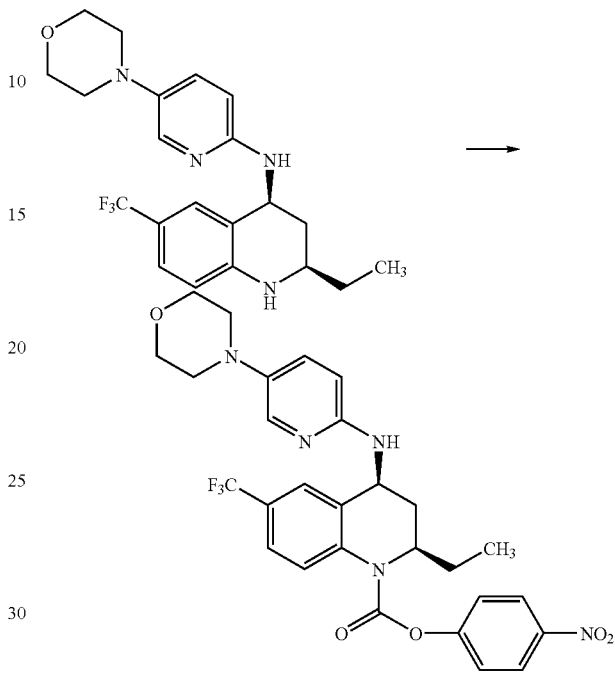

4-Nitrophenyl chloroformate (3.47 g) was added to a solution of (2R,4S)-4-(5-morpholin-4-yl-pyridin-2-yl-amino)-2-ethyl-1,2,3,4-tetrahydroquinoline (1.4 g) dissolved in chlorobenzene (30 ml) and pyridine (1.4 ml) was added dropwise. After being stirred at room temperature overnight, water and chloroform were added to the reaction mixture and the organic layer was separated, washed with 1N hydrochloric acid and a saturated brine, dried over magnesium sulfate and concentrated in vacuo. The resulting residue was purified by column chromatography (NH-silica gel; hexane:ethyl acetate=17:3→3:2) to give the titled compound (1.08 g). MS (m/z): 572 [M+H]$^+$.

(2) (2R,4S)-2-Ethyl-4-(5-morpholin-4-yl-pyridin-2-ylamino)-6-trifluoromethyl-3,4-dihydro-2H-quinolin-1-carboxylic acid 2-tert-butoxycarbonyl-2-methyl-propyl ester

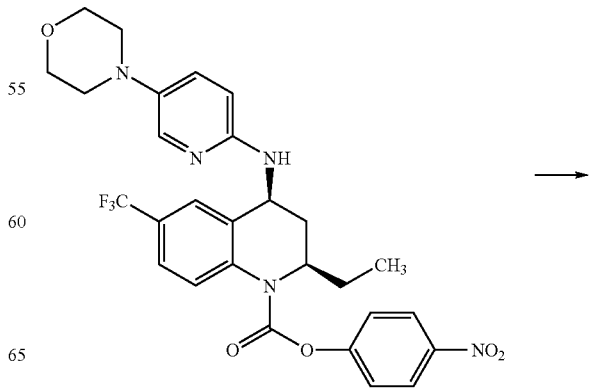

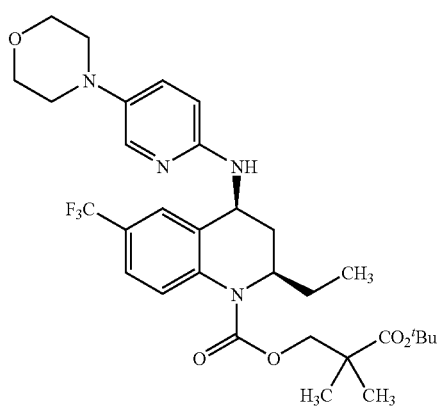

3-Hydroxy-2,2-dimethyl-propionic acid tert-butyl ester (137 mg) and sodium hydride (60%; 32 mg) were added to a solution of the compound obtained in Example 9 (1) (300 mg) dissolved in tetrahydrofuran (5 ml) and stirred at 50° C. for 2 hours. The reaction mixture was cooled to room temperature, a saturated sodium hydrogen carbonate aq. solution and ethyl acetate were added and the organic layer was separated, washed with a saturated brine, dried over magnesium sulfate and concentrated in vacuo. The resulting residue was purified by column chromatography (silica gel; hexane:ethyl acetate=7:3→2:3) to give the titled compound (227 mg). MS (m/z):607 [M+H]$^+$.

Example 10

(2R,4S)-4-[(3,5-Bis-trifluoromethyl-benzyl)-(5-morpholin-4-yl-pyridin-2-yl)-amino]-2-ethyl-6-trifluoromethyl-3,4-dihydro-2H-quinoline-1-carboxylic acid 2-tert-butoxycarbonyl-2-methyl-propyl ester

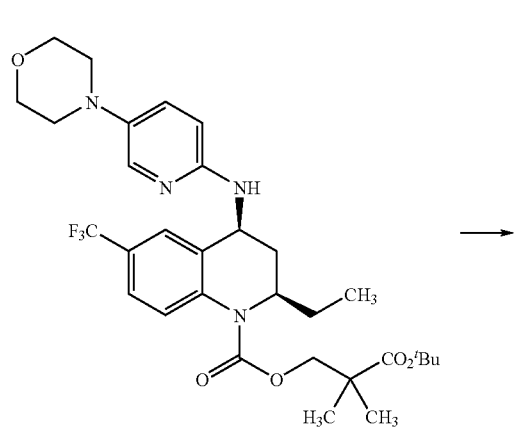

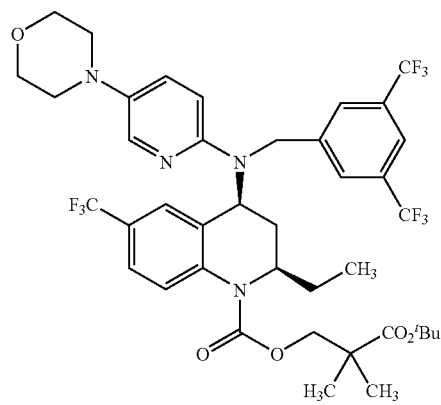

Tetrabutylammonium iodide (53 mg) was added to a solution of the compound obtained in Example 9 (2) above (217 mg) in tert-butyl methyl ether (4 ml) under nitrogen atmosphere at 0° C. 3,5-Bis(trifluoromethyl)benzyl bromide (164 mg) was added dropwise and the solution was stirred for 4.5 hours while the temperature was gradually raised from 0° C. to room temperature. To the reaction mixture, were added with 1N hydrochloric acid and ethyl acetate, and the organic layer was separated, washed with a saturated brine, dried over magnesium sulfate and concentrated in vacuo. The resulting residue was purified by column chromatography (silica gel; hexane:ethyl acetate=19:1→4:1) to give the titled compound (182 mg). MS (m/z): 833 [M+H]$^+$.

Example 11

(2R,4S)-4-[(3,5-Bis-trifluoromethyl-benzyl)-(5-morpholin-4-yl-pyridin-2-yl)-amino]-2-ethyl-6-trifluoromethyl-3,4-dihydro-2H-quinoline-1-carboxylic acid 2-carboxy-2-methyl-propyl ester

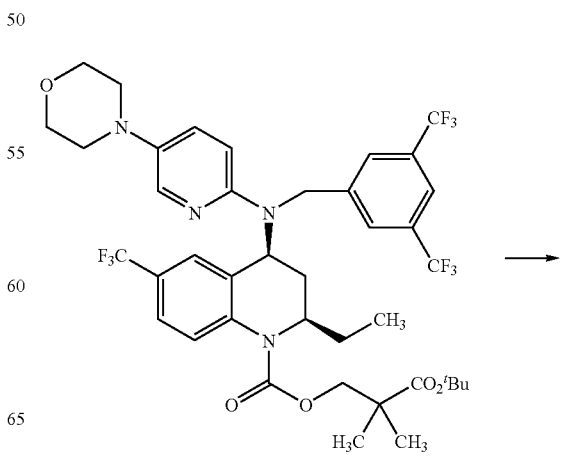

-continued

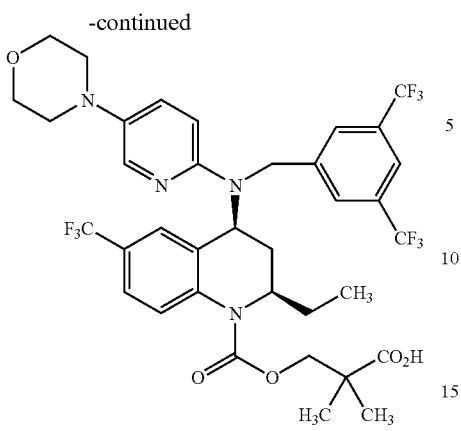

The compound obtained in Example 10 above (178 mg) was dissolved in 4N—HCl/dioxane (2 ml) and stirred at room temperature for 2.5 hours. To the reaction mixture, were added a saturated sodium hydrogen carbonate aq. solution and ethyl acetate and the organic layer was separated, washed with a saturated brine, dried over magnesium sulfate and concentrated in vacuo. The resulting residue was purified by column chromatography (silica gel; chloroform:methanol=1:0→9:1) to give the titled compound (157 mg). MS (m/z): 777 [M+H]$^+$.

Example 12

(2R,4S)-4-(5-Morpholine-4-yl-pyrimidin-2-yl)-amino-2-ethyl-6-trifluoromethyl-1,2,3,4-tetrahydro-quinoline

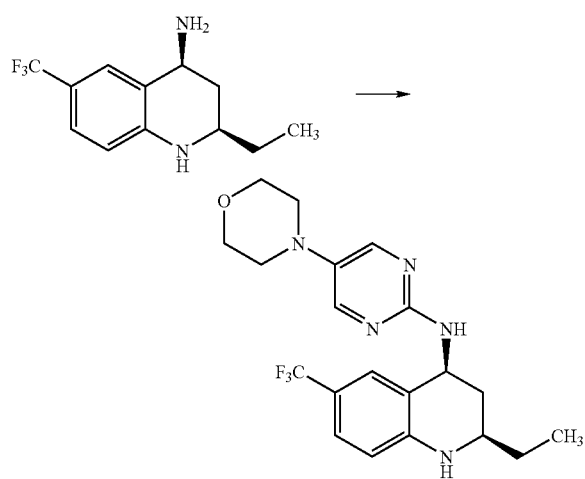

4-(2-Chloro-pyrimidin-5-yl)-morpholine (1.64 g), palladium acetate (150 mg), 2,2'-bis(diphenylphosphino)-1,1'-binaphthyl (460 mg) were dissolved in toluene (5 ml) and stirred under nitrogen atmosphere at 50° C. for 30 minutes. The mixture was cooled to room temperature, thereto was added dropwise (2R,4S)-2-ethyl-6-trifluoromethyl-1,2,3,4-tetrahydroquinolin-4-ylamine (2 g) dissolved in toluene (20 ml) and the solution was stirred at room temperature for 15 minutes. The stirring was continued at 50° C. overnight after addition of sodium tert-butoxide (1.73 g). To the reaction mixture, were added water and ethyl acetate, and the organic layer was separated, washed with a saturated brine, dried over magnesium sulfate and concentrated in vacuo. The resulting residue was purified by column chromatography (silica gel; hexane:ethyl acetate=7:3→2:3) to give the titled compound (1.55 g). MS (m/z): 408 [M+H]$^+$.

Example 13

(2R,4S)-(2-Ethyl-6-trifluoromethyl-1,2,3,4-tetrahydro-quinolin-4-yl)-carbamic acid naphthalen-1-ylmethyl ester

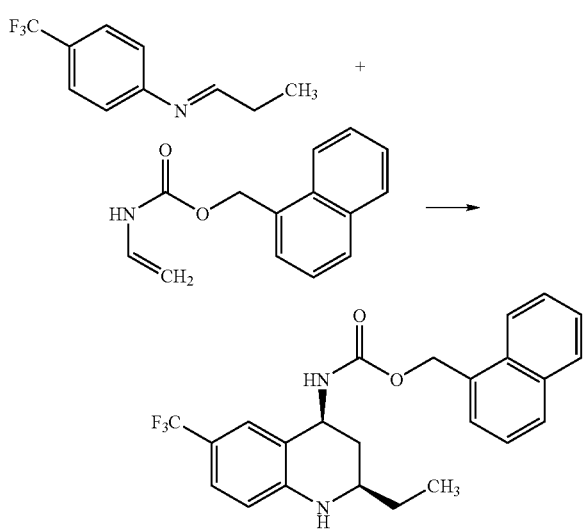

In a flask equipped with a Soxhlet extractor containing 4 Å molecular sieves (pellets), (R)-binaphthol (716 mg) dissolved in dichloromethane (35 ml) was added. To the solution, was added trimethoxyborane (279 μl) and the mixture was heated to reflux under nitrogen atmosphere for 2 hours. The solution was concentrated under nitrogen atmosphere, and the resulting residue was dissolved in dichloromethane to give a dichloromethane solution of a chiral boron catalyst (8.0 ml). Vinyl-carbamic acid naphthalen-1-ylmethyl ester (227 mg) was dissolved in a mixture of toluene (2.5 ml) and dichloromethane (1.5 ml) and a 0.4M propylidene-(4-trifluoromethyl-phenyl)-amine/dichloromethane solution (2.75 ml) was added. Thereto was added the dichloromethane solution of a chiral boron catalyst prepared above (1.6 ml) dropwise under nitrogen atmosphere at 0° C. over 30 minutes. The mixture was stirred at the same temperature for 2 hours, then allowed to warm to room temperature, and the stirring was continued overnight. To the reaction mixture, was added a 0.5N NaOH aq. solution and extracted with ether. The organic layer was washed with a saturated brine twice, dried over magnesium sulfate and concentrated in vacuo. The resulting residue was purified by column chromatography (silica gel; hexane:ethyl acetate=19:1→7:3) to give the titled compound (331 mg). MS (m/z): 429 [M+H]$^+$. Enantioselectivity was 96% ee determined by HPLC using CHIRALPAK IB (DAICEL CHEMICAL INDUSTRIES, LTD.), hexane:ethanol=9:1, flow rate=5 ml/min.

Examples 14-16

The products were obtained with yields and enantioselectivities shown in Table 1 in the same treatment as Example 13 starting the corresponding materials.

TABLE 1

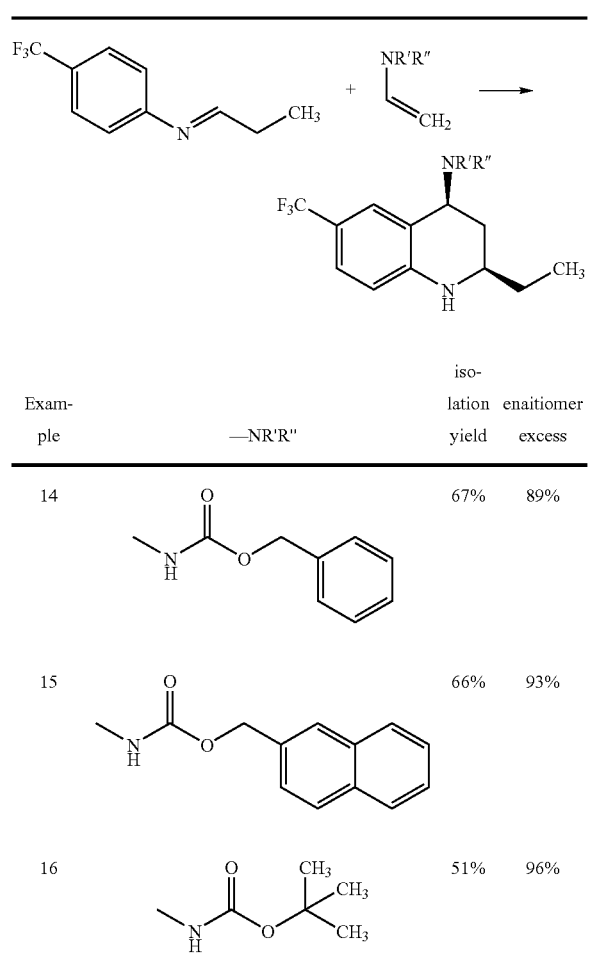

| Example | —NR'R" | isolation yield | enantiomer excess |
|---|---|---|---|
| 14 | | 67% | 89% |
| 15 | | 66% | 93% |
| 16 | | 51% | 96% |

Example 17

(2R,4S)-(2-Ethyl-6-trifluoromethyl-1,2,3,4-tetrahydro-quinolin-4-yl)-carbamic acid naphthalen-1-ylmethyl ester

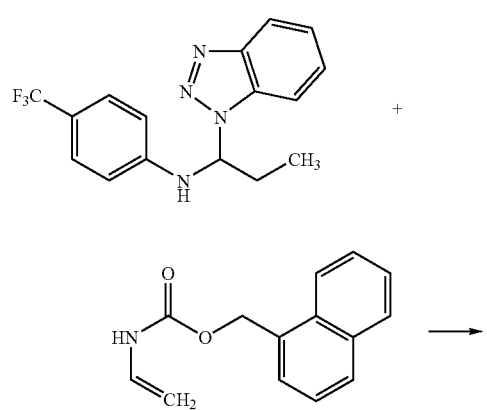

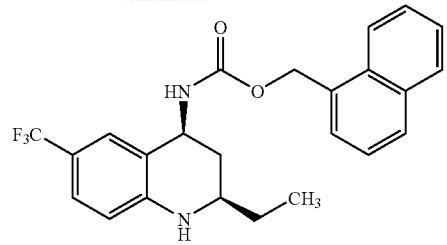

(1-Benzotriazol-1-yl-propyl)-(4-trifluoromethyl-phenyl)-amine (352 mg) was treated in the same manner as Example 13 to give the titled compound (272 mg). MS (m/z): 429 [M+H]$^+$. Enantioselectivity 99% ee

Example 18

(2R,4S)-2-Ethyl-6-trifluoromethyl-1,2,3,4-tetrahydro-quinolin-4-ylamine

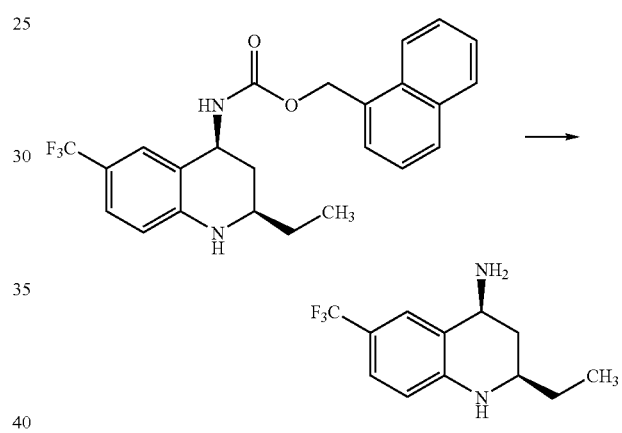

The compound obtained in Example 13 (101 mg) was dissolved in a mixture of methanol (2 ml) and dichloromethane (1 ml), and 10% palladium carbon (100 mg) was added to the solution and the mixture was stirred under hydrogen atmosphere at room temperature for an hour. The mixture was filtered, the filtrate was concentrated in vacuo and the resulting residue was purified by column chromatography (NH-silica gel; hexane:ethyl acetate=4:1→0:1) to give the titled compound (30 mg). MS (m/z):245 [M+H]$^+$, $[\alpha]_D^{23}$:+29.1° (c 1.0, methanol).

Example 19

(R)-2-Ethyl-6-trifluoromethyl-2,3-dihydro-1H-quinolin-4-one O-methyl-oxime

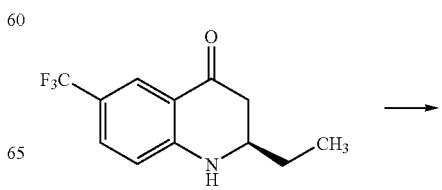

-continued

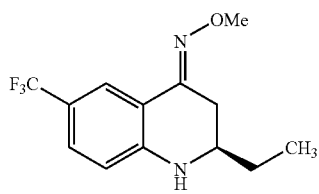

The compound obtained in Example 2 (2) above (2.43 g), methoxyamine hydrochloride (1.25 g), sodium acetate (1.64 g) and water (2.4 ml) were added to tetrahydrofuran (22 ml) and the mixture was stirred at room temperature for about 48 hours. Toluene (24 ml) and water (12 ml) were added to the reaction mixture, the organic layer was separated, and washed with water (12 ml) and a saturated brine (12 ml). The organic layer was concentrated at reduced pressure and the resulting residue was purified by column chromatography and concentrated to give the titled compound as an oily material (1.92 g, yield 71%). MS (APCI) m/z: 273 [M+H]+.

(2) (2R,4S)-2-Ethyl-6-trifluoromethyl-1,2,3,4-tetrahydroquinolin-4-ylamine methanesulfonate

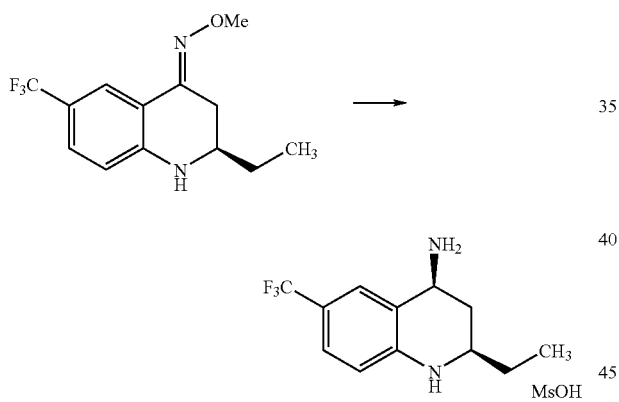

Into a pressure vessel, the compound obtained in Example 19 (1) above (500 mg) was added and dissolved in isopropyl alcohol and 10% palladium carbon (57% wet product; 172 mg) was added. After replacement with nitrogen gas, the gas was replaced with hydrogen gas three times and the mixture was stirred under 5 atms at 40° C. for 4 hours. After the mixture was cooled, the mixture was filtered, the insoluble materials were washed with isopropyl alcohol (1 ml). The filtrate was concentrated at reduced pressure, isopropyl alcohol (1.5 ml) was added to the residue, and then methanesulfonic acid (176 mg) dissolved in isopropyl alcohol (0.5 ml) was added dropwise to the solution. After precipitation, n-heptane (3 ml) was added to the mixture and stirred at 20-30° C. for about 0.5 hour and under ice-cooling for about 0.5 hour. The precipitated crystalline was collected by filtration, and washed with a mixture of n-heptane (0.6 ml) and isopropyl alcohol (0.4 ml). The wet product was dried at reduced pressure at about 40° C. to give the titled compound as a crystalline (532 mg, yield 85%). MS (APCI) m/z: 245 [M+H]+, 228 [M−NH2].

Example 20

(R)-3-(4-Trifluoromethyl-phenylamino)-valeric acid

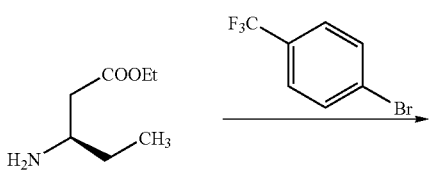

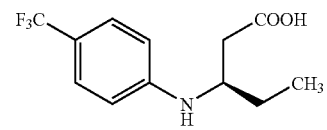

(R)-3-Aminovaleric acid ethyl ester (0.5 g), 4-bromobenzotrifluoride (0.62 g), copper iodide (0.053 g), potassium carbonate (1.14 g) and water (0.5 ml) were added to dimethylformamide (5 ml) and the mixture was sealed under nitrogen atmosphere and stirred at 100° C. for 3 days. The mixture was cooled, water and ethyl acetate were added to the mixture, and the pH of the mixture was adjusted to about 3 or less with addition of 2N HCl. The organic layer was separated, dried over magnesium sulfate and concentrated at reduced pressure. The resulting residue was purified by column chromatography to give the titled compound (0.29 g, yield 40.3%). MS (APCI) m/z: 262 [M+H]+.

Example 21

(1) (2R,4S)-2-Ethyl-4-(5-morpholin-4-yl-pyrimidin-2-ylamino)-6-trifluoromethyl-3,4-dihydro-2H-quinoline-1-carboxylic acid 4-nitrophenyl ester

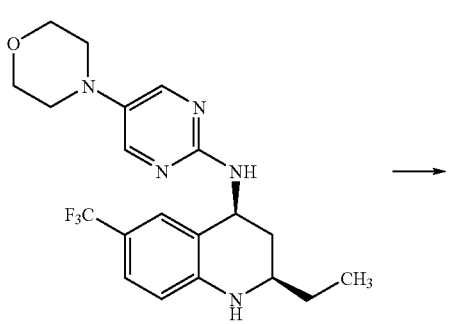

-continued

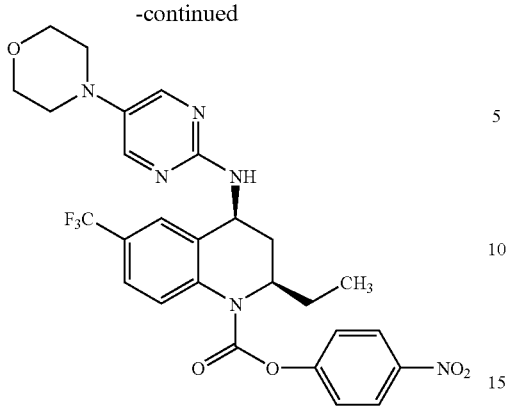

4-Nitrophenyl chloroformate (3.06 g) was added to a solution of the compound obtained in Example 12 above (1.24 g) in chlorobenzene (20 ml), and pyridine (1.03 ml) was added dropwise. After being stirred at room temperature overnight, water and chloroform were added to the reaction mixture, and the organic layer was separated, washed with 1N HCl, a saturated sodium hydrogen carbonate aqueous solution and a saturated brine, dried over magnesium sulfate and concentrated in vacuo. The resulting residue was purified by column chromatography (NH-silica gel; hexane:ethyl acetate=17:3→3:2) to give the titled compound (1.35 g). MS (m/z): 573 [M+H]$^+$.

(2) (2R,4S)-2-Ethyl-4-(5-morpholin-4-yl-pyrimidin-2-ylamino)-6-trifluoromethyl-3,4-dihydro-2H-quinoline-1-carboxylic acid tert-butoxycarbonylmethyl ester

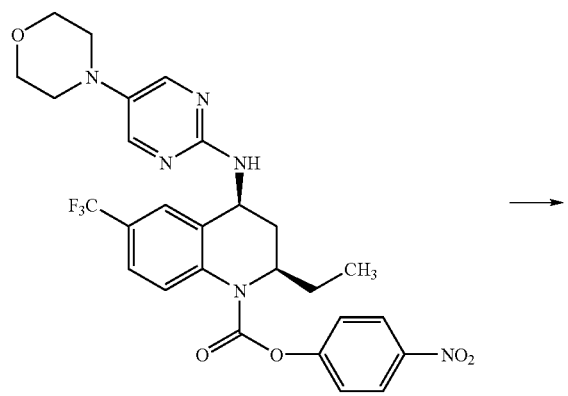

Hydroxyacetic acid tert-butyl ester (70 mg) and sodium hydride (60%; 21 mg) were added to a solution of the compound obtained in Example 21 (1) above (200 mg) in tetrahydrofuran (3 ml) and the mixture was stirred at 50° C. for an hour. The reaction mixture was cooled to room temperature, a saturated sodium hydrogen carbonate aqueous solution and ethyl acetate were added and the organic layer was separated, washed with a saturated brine, dried over magnesium sulfate and concentrated in vacuo. The resulting residue was purified by column chromatography (NH-silica gel; hexane:ethyl acetate=9:1→3:2) to give the titled compound (183 mg). MS (m/z): 566 [M+H]$^+$.

Example 22

(2R,4S)-4-[(3-Cyano-5-trifluoromethyl-benzyl)-(5-morpholin-4-yl-pyrimidin-2-yl)-amino]-2-ethyl-6-trifluoromethyl-3,4-dihydro-2H-quinoline-1-carboxylic acid tert-butoxycarbonylmethyl ester

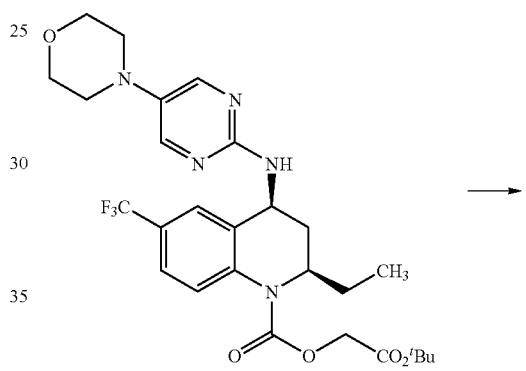

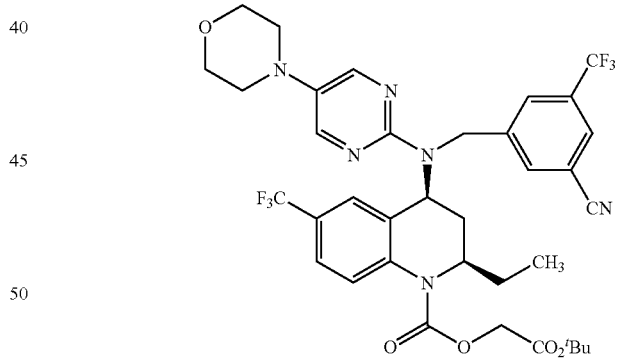

The compound obtained in Example 21 (2) above (177 mg) was dissolved in tert-butyl methyl ether (3 ml) under nitrogen atmosphere and the solution was cooled to 0° C. Thereto were added tetrabutylammonium iodide (46 mg), potassium tert-butoxide (105 mg) and 3-Bromomethyl-5-trifluoromethyl-benzonitrile (124 mg), and the mixture was stirred for 2 hours. 1N HCl and ethyl acetate were added to the reaction mixture and the organic layer was separated, washed with a saturated brine, dried over magnesium sulfate and concentrated in vacuo. The resulting residue was purified by column chromatography (NH-silica gel; hexane:ethyl acetate=4:1→3:2) to give the titled compound (39 mg). MS (m/z): 749 [M+H]$^+$.

Example 23

(2R,4S)-4-[(3-Cyano-5-trifluoromethyl-benzyl)-(5-morpholin-4-yl-pyrimidin-2-yl)-amino]-2-ethyl-6-trifluoromethyl-3,4-dihydro-2H-quinoline-1-carboxylic acid carboxymethyl ester

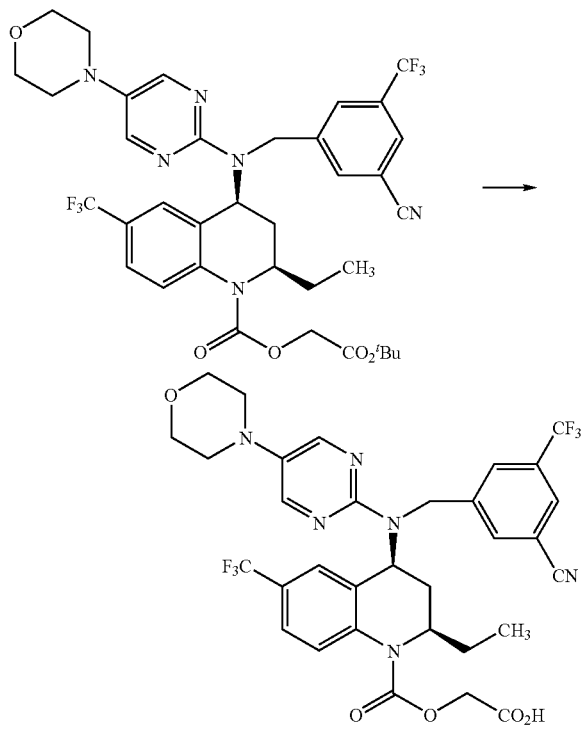

The compound obtained in Example 22 above (37 mg) was dissolved in 4N HCl/dioxane (2 ml) and stirred at room temperature for 6.5 hours. A saturated sodium hydrogen carbonate aqueous solution and ethyl acetate were added to the reaction mixture and the organic layer was separated, washed with a saturated brine, dried over magnesium sulfate and concentrated in vacuo. The resulting residue was purified by column chromatography (silica gel; chloroform:methanol=1:0→17:3) to give the titled compound (26 mg). MS (m/z): 693 [M+H]$^+$.

Reference Example 1

(1) Trifluoroacetic acid anhydride (7.7 ml) was added dropwise to a solution of 5-bromovaleric acid (5 g) in tetrahydrofuran (25 ml) under nitrogen atmosphere at −40° C. and the solution was stirred at −40° C. for 30 minutes. To the mixture, was added tert-butanol (25 ml) at −40° C. and the stirring was continued for 3 hours while the temperature was gradually raised up to room temperature. Water and ethyl acetate were added to the mixture and the organic layer was separated, washed with a saturated sodium hydrogen carbonate aq. solution three times and then a saturated brine, dried over magnesium sulfate and concentrated in vacuo to give 5-bromovaleric acid tert-butyl ester (5.88 g). MS (m/z): 237/239 [M+H]$^+$.

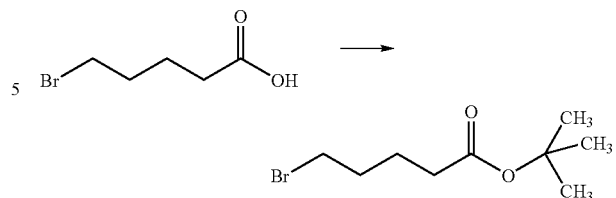

(2) Potassium carbonate (2.54 g) was added to a solution of 5-bromovaleric acid tert-butyl ester (4.3 g) obtained in Reference Example 1 (1) above and 2-chloropyrimidin-5-ol (2 g) in dimethylsulfoxide (8.6 ml) and the mixture was stirred at 40° C. overnight. The reaction mixture was cooled to room temperature, water and ethyl acetate were added and the organic layer was separated, washed with a saturated brine, dried over magnesium sulfate and concentrated in vacuo. The resulting residue was purified by column chromatography (silica gel; hexane:ethyl acetate=49:1→9:1) to give 5-(2-chloropyrimidin-5-yloxy)valeric acid tert-butyl ester (3.82 g). MS (m/z): 287/289 [M+H]$^+$.

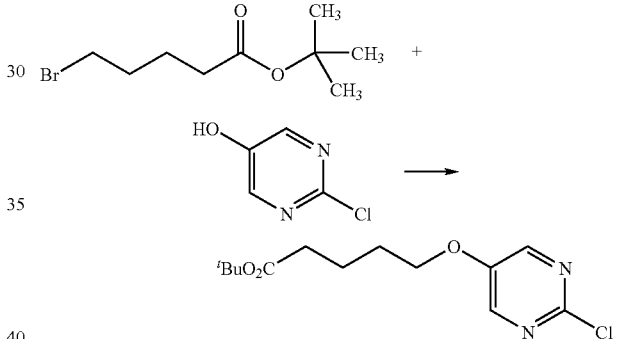

Reference Example 2

4-(6-Bromo-pyridin-3-yl)-morpholine

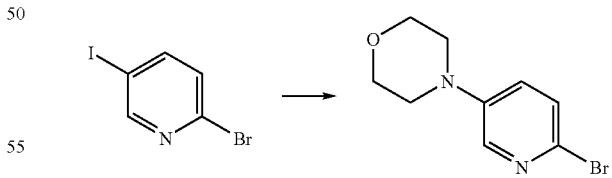

Tris(dibenzylideneacetone)dipalladium (840 mg) and 4,5-bis(diphenyl-phosphino)-9,9-dimethylxanthene (1.6 g) and sodium tert-butoxide (6.6 g) were added to a solution of morpholine (2 ml) and 2-bromo-5-iodo-pyridine (7.8 g) in toluene (230 ml), and the mixture was stirred under nitrogen atmosphere at room temperature overnight. Water and ethyl acetate were added to the mixture and the organic layer was separated, washed with a saturated brine, dried over magnesium sulfate and concentrated in vacuo. The resulting residue was purified by column chromatography (silica gel; hexane:ethyl acetate=9:1→7:3) to give the titled compound (5.07 g). MS (m/z): 243/245 [M+H]+.

Reference Example 3

(1) tert-Butyl methyl 2,2-dimethyl-malonate

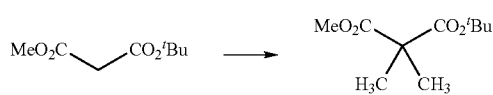

Sodium hydride (60%; 500 mg) was added to a solution of tert-butyl methyl malonate (1 g) in tetrahydrofuran (50 ml) and the mixture was stirred at 0° C. for 10 minutes. Methyl iodide (0.78 ml) was added to the mixture and the stirring was continued for 3 hours. A saturated brine and ethyl acetate were added to the mixture and the organic layer was separated, dried over magnesium sulfate and concentrated in vacuo to give the titled compound (1.12 g). MS (m/z):147 [M+H]+.

(2) 3-Hydroxy-2,2-dimethyl-propionic acid tert-butyl ester

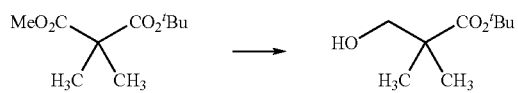

1M lithium tri-tert-butoxy-aluminohydride/tetrahydrofuran solution (14 ml) was added dropwise to a solution of tert-butyl methyl 2,2-dimethyl-malonate (1.12 g) in tetrahydrofuran (30 ml) under nitrogen atmosphere over 15 minutes and the mixture was heated to reflux for 2 hours. The reaction mixture was cooled to room temperature, a saturated ammonium chloride aq. solution and ethyl acetate were added and the organic layer was separated, washed with water and a saturated brine, dried over magnesium sulfate and concentrated in vacuo to give the titled compound (800 mg). MS (m/z): 175 [M+H]+.

Reference Example 4

(1) 2-Benzyloxy-5-bromo-pyrimidine

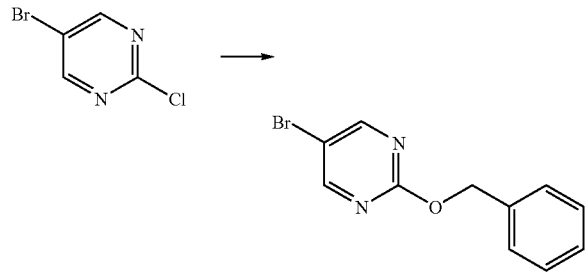

Potassium tert-butoxide (6.96 g) was added to a solution of 5-bromo-2-chloro-pyrimidine (10 g) and benzyl alcohol (6.4 ml) in N,N-dimethylformamide (140 ml) and the mixture was stirred at room temperature for 1.5 hours. Water was added to the mixture and the precipitated solid was collected by filtration, washed with methanol, dried to give the titled compound (10.6 g). MS (m/z): 265/267 [M+H]+.

(2) 4-(2-Benzyloxy-pyrimidin-5-yl)-morpholine

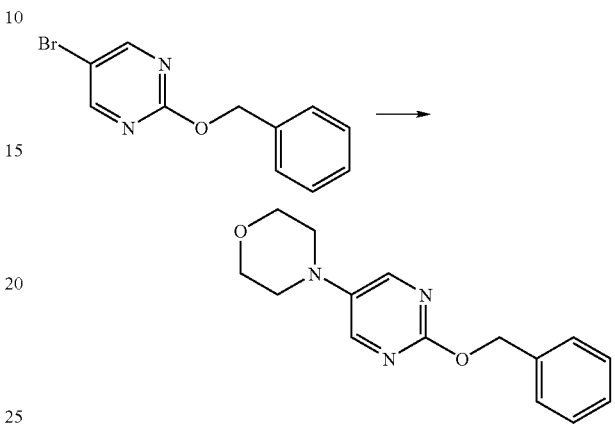

Tris(dibenzylideneacetone)dipalladium (1.78 g), 2-(di-tert-butylphosphino)-biphenyl (2.32 g) and sodium tert-butoxide (4.49 g) were added to a solution of 2-benzyloxy-5-bromo-pyrimidine (10.3 g) and morpholine (4.1 ml) in toluene (180 ml) and the mixture was stirred under nitrogen atmosphere at 50° C. for an hour. The reaction mixture was cooled to room temperature. Water and ethyl acetate were added and the organic layer was separated, washed with a saturated brine, dried over magnesium sulfate and concentrated in vacuo. The residue was triturated with ethyl acetate and hexane to give the titled compound (9.12 g). MS (m/z): 272 [M+H]+.

(3) 5-Morpholin-4-yl-pyrimidin-2-ol hydrochloride

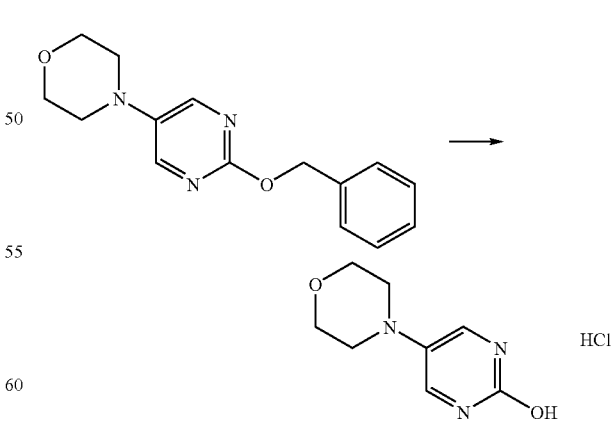

4N—HCl/dioxane (100 ml) was added to 4-(2-benzyloxy-pyrimidin-5-yl)-morpholine (8.4 g) and the resulting suspension was stirred at 50° C. for an hour. The reaction mixture was cooled to room temperature and the precipitated solid was collected by filtration, washed with hexane, dried to give the titled compound (7.49 g). MS (m/z): 182 [M+H]+.

(4) 4-(2-chloro-pyrimidin-5-yl)-morpholine

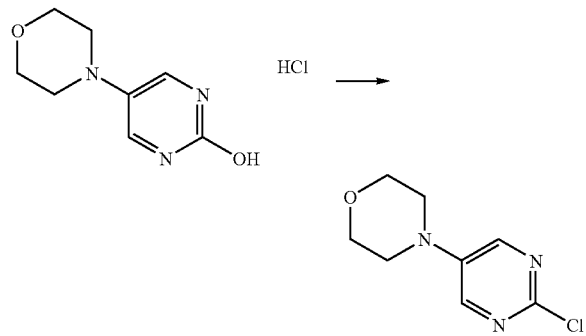

Phosphoryl chloride (16 ml) was added to a solution of 5-morpholin-4-yl-pyrimidin-2-ol hydrochloride (7.49 g) and diethylaniline (11 ml) in acetonitrile (150 ml) over 10 minutes and the mixture was heated to reflux for 7.5 hours. The reaction mixture was cooled to room temperature, and added to a mixture of a saturated sodium hydrogen carbonate aq. solution and chloroform. The organic layer was washed with a saturated brine, dried over magnesium sulfate and concentrated in vacuo. The resulting residue was purified by column chromatography (silica gel; hexane:ethyl acetate=4:1→1:1) to give the titled compound (4.6 g). MS (m/z): 200/202 [M+H]+.

Reference Example 5

Vinyl-carbamic acid naphthalen-1-ylmethyl ester

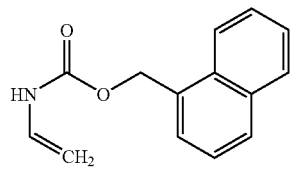

Acryloyl chloride (5.4 ml) dissolved in toluene (20 ml) was added dropwise to an aqueous solution (33 ml) of sodium azide (5.17 g) at 0° C. and the mixture was stirred at the same temperature for 45 minutes. After the mixture was warmed up to room temperature, a saturated sodium hydrogen carbonate aq. solution was added and the organic layer was washed with a saturated brine, dried over magnesium sulfate. The resulting toluene solution was diluted to a volume of 67 ml with an addition of toluene. The toluene solution (54 ml) was added to a mixture of naphthalen-1-yl-methanol (5.67 g), pyridine (1.45 ml), hydroquinone (197 mg) and toluene (11 ml) at 85° C. and the mixture was stirred at the same temperature for 1.5 hours. The reaction mixture was allowed to cool to room temperature, a saturated sodium hydrogen carbonate aqueous solution and ethyl acetate were added, and the organic layer was washed with a saturated brine, dried over magnesium sulfate, and concentrated in vacuo. Isopropyl alcohol and hexane were added to the resulting residue, the insoluble materials were filtered off and the filtrate was concentrated again in vacuo. The resulting residue was purified by column chromatography (silica gel; hexane:ethyl acetate=4:1→1:1) to give the titled compound (3.28 g). MS (m/z): 245 [M+NH4]+.

Reference Example 6

3-Bromomethyl-5-trifluoromethyl-benzonitrile

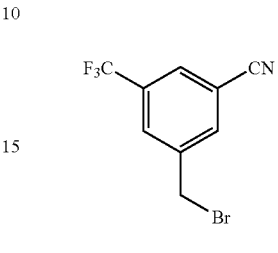

(1) 3-Nitro-5-(trifluoromethyl)benzoic acid (50 g) is dissolved in tetrahydrofuran (300 ml) and thereto is added dropwise a 1.0M-borane tetrahydrofuran complex/tetra-hydrofuran (300 ml) at 0° C. under nitrogen atmosphere over 2 hours and the mixture is stirred at 75° C. for 1 hour and a half. The reaction solution is allowed cool to room temperature and concentrated under reduced pressure, and thereto is added a 1N-hydrochloric acid and the mixture is extracted with ethyl acetate. The organic layer is washed successively with water and a saturated brine, dried over magnesium sulfate, and concentrated under reduced pressure to give crude (3-nitro-5-trifluoromethyl-phenyl)-methanol. This product is dissolved in methanol (500 mL) and thereto is added 10% palladium-carbon (5 g) and the mixture is stirred under hydrogen atmosphere at room temperature overnight. The catalyst is removed by filtration, and the filtrate is concentrated under reduced pressure to give crude (3-amino-5-trifluoromethyl-phenyl)-methanol. To copper (II) bromide (53.6 g) is added acetonitrile (500 ml), followed by an addition dropwise of tert-butyl nitrite (35.7 ml) under ice-cooling and the mixture is stirred under nitrogen atmosphere for 5 minutes. To reaction mixture is added dropwise a solution of the above crude (3-amino-5-trifluoromethyl-phenyl)-methanol in acetonitrile (200 ml) under ice-cooling over 1 hour and 15 minutes and the mixture is stirred at room temperature under nitrogen atmosphere overnight. To reaction mixture is added a 1N-hydrochloric acid and the mixture is extracted with ethyl acetate. The organic layer is washed successively with a 1N-hydrochloric acid, water and a saturated brine, dried over magnesium sulfate, and concentrated under reduced pressure. The resulting residue is purified by silica gel column chromatography (hexane:ethyl acetate=7:1→4:1) to give (3-bromo-5-trifluoromethyl-phenyl)-methanol (40.7 g). NMR (CDCl3): 1.90 (1H, t), 4.76 (2H, d), 7.56 (1H, s), 7.68 (1H, s), 7.72 (1H, s).

(2) (3-Bromo-5-trifluoromethyl-phenyl)-methanol (33.9 g) is dissolved in N,N-dimethylformamide (400 mL) and thereto are added zinc (II) cyanide (16.39 g) and tetrakis(triphenylphosphine)palladium (7.68 g) and the mixture is heated under nitrogen atmosphere at 120° C. for 2 hours. The reaction solution is allowed cool to room temperature, and filtered through Celite™, and the filtrate is concentrated under reduced pressure. Thereto is added water and the mixture is extracted with ethyl acetate. The organic layer is washed with a saturated brine, dried over sodium sulfate, and concentrated under reduced pressure. The resulting residue is purified by silica gel column chromatography (hexane:ethyl acetate=2:1)

to give 3-hydroxymethyl-5-trifluoromethyl-benzonitrile (23.4 g). NMR (CDCl$_3$): 2.09 (1H, t), 4.85 (2H, d), 7.83 (1H, s), 7.87 (2H, s).

(3) 3-Hydroxymethyl-5-trifluoromethyl-benzonitrile (23.4 g) is dissolved in methylene chloride (230 mL) and thereto is added carbon tetrabromide (42.4 g), followed by an addition of triphenylphosphine (32.0 g) under ice-cooling and the mixture is stirred at the same temperature for 30 minutes. The reaction solution is concentrated under reduced pressure. The resulting residue is purified by silica gel column chromatography (hexane:ethyl acetate=10:1) to give 3-bromomethyl-5-trifluoromethyl-benzonitrile (25.5 g). NMR (CDCl$_3$): 4.51 (2H, s), 7.86 (1H, s), 7.88 (2H, s).

INDUSTRIAL APPLICABILITY

The present invention is useful to prepare optically active tetrahydroquinoline derivatives which can be used for the treatment and/or prevention of diseases such as arteriosclerotic diseases, hyperlipidemia, dyslipidemia and the like, wherein an inhibitor of CETP is effective, and to prepare synthetic intermediates thereof.

The invention claimed is:

1. A process for preparing (2R,4S)-2-ethyl-6-trifluoromethyl-1,2,3,4-tetrahydro-quinolin-4-ylamine shown in the formula I-a:

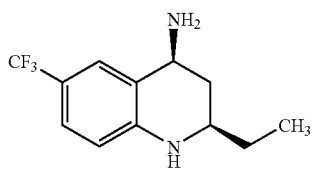

or a salt thereof, comprising catalytic reduction of (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime in the presence of a palladium catalyst, followed by conversion of the product into a salt thereof, if desired.

2. A process for preparing (2R,4S)-2-ethyl-6-trifluoromethyl-1,2,3,4-tetrahydroquinolin-4-ylamine or a salt thereof, comprising the steps of:
(a) reacting (R)-3-aminovaleric acid or its alkyl ester with a compound of the formula I-f:

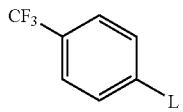

wherein L means a leaving group, to form (R)-3-(4-trifluoromethyl-phenylamino)-valeric acid;
(b) reacting (R)-3-(4-trifluoromethyl-phenylamino)-varelic acid with phosphorus pentoxide to form (R)-2-ethyl-6-trifluoromethyl-2,3-dihydro-1H-quinolin-4-one;
(c) converting (R)-2-ethyl-6-trifluoromethyl-2,3-dihydro-1H-quinolin-4-one into (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime; and (d) carrying out a catalytic reduction of (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-alkyl-oxime in the presence of a palladium catalyst, followed by conversion of the product into a salt thereof, if desired.

3. A process for preparing (2R,4S)-2-ethyl-6-trifluoromethyl-1,2,3,4-tetrahydroquinolin-4-ylamine or a salt thereof, comprising asymmetric cyclization reaction of propylidene-(4-trifluoromethyl-phenyl)-amine or its equivalent with an optionally protected vinyl amine shown in the general formula I-g:

wherein R' and R'' are the same or different, and hydrogen or an amino-protecting group, or R' and R'' combine together to form an amino-protecting group,
in the presence of optically active acid catalyst to prepare a compound of the general formula I-h:

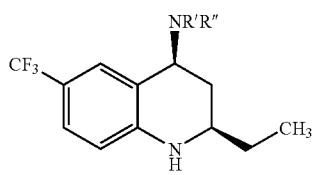

wherein the symbols have the same meaning as above, and followed by deprotecting the product, if necessary, and converting the product into a salt thereof, if desired.

4. A process for preparing a compound shown in the formula I:

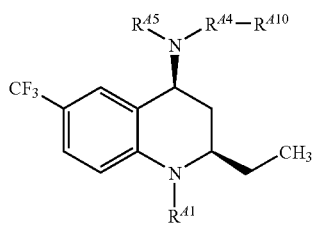

wherein $R^{41}$ is a hydrogen atom, an optionally substituted alkoxycarbonyl group, an optionally substituted carbamoyl group, an optionally substituted alkyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), or a saturated or unsaturated monocyclic or bicyclic heterocyclic carbonyl group containing 1 to 4 heteroatom(s) selected independently from oxygen, sulfur and nitrogen atoms (the heterocyclic group is optionally substituted);
$R^{44}$ is an optionally substituted alkylene group;
$R^{45}$ is a saturated or unsaturated monocyclic or bicyclic heterocyclic group containing 1 to 4 heteroatom(s)

selected independently from oxygen, sulfur and nitrogen atoms, wherein the said heterocyclic group is substituted by 1 to 5 substituent(s) selected from the following groups, or the said heterocyclic group is substituted by 1 to 5 substituent(s) selected from the following groups and further by a halogen atom, an oxo and/or hydroxyl group:

a cyano group, a nitro group, a carboxyl group, a sulfo group, a $C_{3-10}$ alkyl group, a substituted alkyl group, an optionally substituted cycloalkyl group, an optionally substituted alkenyl group, a $C_{3-10}$ alkoxy group, a substituted alkoxy group, an optionally substituted cycloalkoxy group, an optionally substituted alkoxycarbonyl group, an optionally substituted carbamoyl group, an optionally substituted carbamimidoyl group, an optionally substituted alkylthio group, an optionally substituted alkylsulfinyl group, an optionally substituted alkylsulfonyl group, an optionally substituted amino group, an optionally substituted sulfamoyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), a saturated or unsaturated monocyclic or bicyclic heterocyclic oxy group containing 1 to 4 heteroatom(s) selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatom(s) selected independently from oxygen, sulfur and nitrogen atoms (the heterocyclic carbonyl group is optionally substituted); and $R^{410}$ is an aromatic ring optionally containing 1 to 3 heteroatom(s) selected independently from oxygen, sulfur and nitrogen atoms (the aromatic ring is optionally substituted), or a pharmaceutically acceptable salt thereof;

comprising preparing (2R,4S)-2-ethyl-6-trifluoromethyl-1,2,3,4-tetrahydroquinolin-4-ylamine or a salt thereof, according to the process of claim 1, 2 or 3, and introducing —$R^{45}$, —$R^{41}$, and —$R^{44}$—$R^{410}$ respectively, followed by conversion of the product into a pharmaceutically acceptable salt thereof, if desired.

5. A process for preparing a compound shown in the formula I:

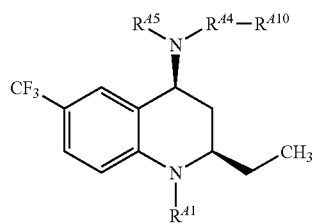

wherein $R^{41}$ is a hydrogen atom, an optionally substituted alkoxycarbonyl group, an optionally substituted carbamoyl group, an optionally substituted alkyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), or a saturated or unsaturated monocyclic or bicyclic heterocyclic carbonyl group containing 1 to 4 heteroatom(s) selected independently from oxygen, sulfur and nitrogen atoms (the heterocyclic group is optionally substituted);

$R^{44}$ is an optionally substituted alkylene group;

$R^{45}$ is a saturated or unsaturated monocyclic or bicyclic heterocyclic group containing 1 to 4 heteroatom(s) selected independently from oxygen, sulfur and nitrogen atoms, wherein the said heterocyclic group is substituted by 1 to 5 substituent(s) selected from the following groups, or the said heterocyclic group is substituted by 1 to 5 substituent(s) selected from the following groups and further by a halogen atom, an oxo and/or hydroxyl group:

a cyano group, a nitro group, a carboxyl group, a sulfo group, a $C_{3-10}$ alkyl group, a substituted alkyl group, an optionally substituted cycloalkyl group, an optionally substituted alkenyl group, a $C_{3-10}$ alkoxy group, a substituted alkoxy group, an optionally substituted cycloalkoxy group, an optionally substituted alkoxycarbonyl group, an optionally substituted carbamoyl group, an optionally substituted carbamimidoyl group, an optionally substituted alkylthio group, an optionally substituted alkylsulfinyl group, an optionally substituted alkylsulfonyl group, an optionally substituted amino group, an optionally substituted sulfamoyl group, an optionally substituted alkanoyl group, a saturated or unsaturated monocyclic or bicyclic heterocyclic group containing 1 to 4 heteroatom(s) selected independently from oxygen, sulfur and nitrogen atoms (the heterocyclic group is optionally substituted), a saturated or unsaturated monocyclic or bicyclic heterocyclic oxy group containing 1 to 4 heteroatom(s) selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatom(s) selected independently from oxygen, sulfur and nitrogen atoms (the heterocyclic carbonyl group is optionally substituted); and $R^{410}$ is an aromatic ring optionally containing 1 to 3 heteroatom(s) selected independently from oxygen, sulfur and nitrogen atoms (the aromatic ring is optionally substituted), or a pharmaceutically acceptable salt thereof, comprising preparing (2R,4S)-2-ethyl-6-trifluoromethyl-1,2,3,4-tetrahydroquinolin-4-yl-amine or a salt thereof according to the process of claim 1, 2 or 3, and introducing —$R^{45}$ at first and then —$R^{41}$ and —$R^{44}$—$R^{410}$ respectively, followed by conversion of the product into a pharmaceutically acceptable salt thereof, if desired.

6. A process for preparing a compound of the general formula II:

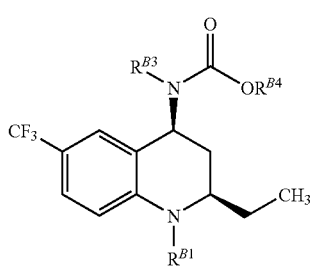

II wherein $R^{B1}$ is hydrogen, $Y^B$, $W^B$—$X^B$ or $W^B$—$Y^B$; $W^B$ is carbonyl, thiocarbonyl, sulfinyl or sulfonyl; $X^B$ is —O—$Y^B$, —S—$Y^B$, —N(H)—$Y^B$ or —N($Y^B$)$_2$; and $Y^B$ in each case is independently $Z^B$ or a fully saturated, partially unsaturated or fully unsaturated straight or branched carbon chain having 1 to 10 member(s), wherein the said carbon atom except a linker may be replaced with one or two heteroatom(s) selected independently from oxygen, sulfur and nitrogen; and the said carbon atom may be mono-, di- or tri-substituted with halogen, the said carbon atom may be mono-substituted with hydroxyl and the said carbon atom may be mono-substituted with oxo;

the said sulfur may be mono- or di-substituted with oxo;

the said nitrogen may be mono- or di-substituted with oxo; and the said carbon chain may be mono-substituted with $Z^B$;

$Z^B$ is a partially saturated, fully saturated or fully unsaturated 3- to 8-membered ring which may contain 1 to 4 heteroatom(s) selected independently from oxygen, sulfur and nitrogen, or a bicyclic ring optionally containing 1 to 4 heteroatom(s) selected independently from nitrogen, sulfur and oxygen, wherein two partially saturated, fully saturated or fully unsaturated 3- to 6-membered rings are fused; and the $Z^B$ group may be substituted independently with 1, 2, or 3 substituent(s) selected from halo, (C$_2$-C$_6$)alkenyl, (C$_1$-C$_6$)alkyl, hydroxyl, (C$_1$-C$_6$)alkoxy, (C$_1$-C$_4$)alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$)alkylamino; the said (C$_1$-C$_6$)alkyl substituent may be substituted independently with 1, 2, or 3 substituent(s) selected from halo, hydroxyl, (C$_1$-C$_6$)alkoxy, (C$_1$-C$_4$)alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$)alkylamino; and the said (C$_1$-C$_6$)alkyl substituent may be substituted with 1- to 9 fluorine;

$R^{B3}$ is hydrogen or $Q^B$; $Q^B$ is a fully saturated, partially unsaturated or fully unsaturated straight or branched carbon chain having 1 to 6 member(s), wherein the carbon atom except a linker may be replaced with one heteroatom selected independently from oxygen, sulfur and nitrogen; and the said carbon atom may be mono-, di- or tri-substituted with halo, the said carbon atom may be mono-substituted with hydroxyl, and the said carbon atom may be mono-substituted with oxo; the said sulfur may be mono- or di-substituted with oxo;

the said nitrogen may be mono- or di-substituted with oxo; and the said carbon chain may be mono-substituted with $V^B$;

$V^B$ is a partially saturated, fully saturated or fully unsaturated 3- to 8-membered ring which may contain 1 to 4 heteroatom(s) selected independently from oxygen, sulfur and nitrogen, or a bicyclic ring optionally containing 1 to 4 heteroatom(s) selected independently from nitrogen, sulfur and oxygen, wherein two partially saturated, fully saturated or fully unsaturated 3- to 6-membered rings are fused;

the said $V^B$ group may be substituted with 1, 2, or 3 substituent(s) selected from halo, (C$_1$-C$_6$)alkyl, (C$_2$-C$_6$)alkenyl, hydroxyl, (C$_1$-C$_6$)alkoxy, (C$_1$-C$_4$)alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$)alkylamino;

the said (C$_1$-C$_6$)alkyl and (C$_2$-C$_6$)alkenyl group may be substituted with 1, 2 or 3 substituent(s) selected from hydroxyl, (C$_1$-C$_6$)alkoxy, (C$_1$-C$_4$)alkylthio, amino, nitro, cyano, oxo, carboxy, (C$_1$-C$_6$)alkyloxycarbonyl, mono-N—(C$_1$-C$_6$)alkylamino, and di-N,N—(C$_1$-C$_6$) alkylamino; the said (C$_1$-C$_6$)alkyl and (C$_2$-C$_6$)alkenyl group may be substituted with 1 to 9 fluorine;

$R^{B4}$ is $Q^{B1}$ or $V^{B1}$; $Q^{B1}$ is a fully saturated, partially unsaturated or fully unsaturated straight or branched carbon chain having 1 to 6 member(s), wherein the carbon atom except a linker may be replaced with one heteroatom selected independently from oxygen, sulfur and nitrogen; and the said carbon may be mono-, di- or tri-substituted with halo, the said carbon may be mono-substituted with hydroxyl, and the said carbon may be mono-substituted with oxo;

the said sulfur may be mono- or di-substituted with oxo;

the said nitrogen may be mono- or di-substituted with oxo; and the said carbon chain may be mono-substituted with $V^{B1}$;

$V^{B1}$ is a partially saturated, fully saturated or fully unsaturated 3- to 6-membered ring which may contain 1 to 2 heteroatom(s) selected independently from nitrogen, sulfur and oxygen; the said $V^{B1}$ group may be substituted with 1, 2, 3 or 4 substituent(s) selected from halo, (C$_1$-C$_6$)alkyl, (C$_1$-C$_6$)alkoxy, amino, nitro, cyano, (C$_1$-C$_6$)alkyloxycarbonyl, mono-N—(C$_1$-C$_6$) alkylamino, and di-N,N—(C$_1$-C$_6$)alkylamino; the said (C$_1$-C$_6$)alkyl group may be mono-substituted with oxo; the said (C$_1$-C$_6$)alkyl group may be substituted with 1 to 9 fluorine;

provided that $R^{B3}$ must include $V^B$ or $R^{B4}$ must include $V^{B1}$, a prodrug thereof, or a pharmaceutically acceptable salt of said compound or of said prodrug, comprising preparing (2R,4S)-2-ethyl-6-trifluoromethyl-1,2,3,4-tetrahydroquinolin-4-yl-amine or a salt thereof according to the process of claim 1, 2, or 3, and introducing —$R^{B1}$, —COOR$^{B4}$ and —$R^{B3}$, followed by conversion of the product into a prodrug thereof, or a pharmaceutically acceptable salt of said compound or of said prodrug, if desired.

7. A process for preparing a compound of the general formula III:

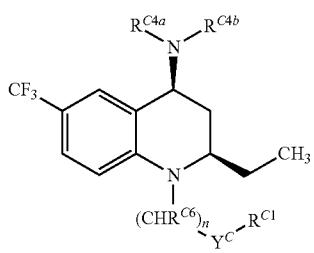

wherein n is 0, 1, 2 or 3; $Y^C$ is a single bond, C=O or —S(O)$_t$ and t is 0, 1 or 2;

$R^{C1}$ is a group selected from hydroxyl, (C$_1$-C$_6$)alkyl, aryl, (C$_2$-C$_6$)alkenyl, (C$_1$-C$_6$)-haloalkyl, (C$_1$-C$_6$)alkylheterocyclic, (C$_3$-C$_8$)cycloalkyl, (C$_1$-C$_6$)alkylcycloalkyl, (C$_1$-C$_6$)-alkylaryl, heterocyclyl, (C$_1$-C$_6$)alkylalcohol, (C$_1$-C$_6$)alkoxy, aryloxy, —O(C$_2$-C$_6$)alkenyl, —O(C$_1$-C$_6$)haloalkyl, —O(C$_1$-C$_6$)alkylheterocyclic, —O(C$_3$-C$_8$)cycloalkyl, —O(C$_1$-C$_6$)alkyl-cycloalkyl, —NR$^{C7}$R$^{C8}$ and —O(C$_1$-C$_6$)alkylaryl, —O-heterocyclic, —O(C$_1$-C$_6$)alkylhetero-cyclic, (C$_1$-C$_6$)alkyl-O—C(O)NR$^{C7}$R$^{C8}$, (C$_1$-C$_6$)alkyl-NR$^{C7}$C(O)NR$^{C7}$R$^{C8}$, and (C$_0$-C$_6$)-alkyl-COOR$^{C11}$;

provided that $R^{C1}$ is not hydroxyl when $Y^C$ is —S(O)$_t$; and the cycloalkyl, the aryl and the heterocyclic may be substituted with 1 to 3 substituent(s) selected independently from oxo, hydroxyl, halo, (C$_1$-C$_6$)alkyl, (C$_2$-C$_6$)alkenyl, (C$_2$-C$_6$)alkynyl, (C$_1$-C$_6$)alkoxy, (C$_1$-C$_6$)haloalkyl, (C$_1$-C$_6$)alkylalcohol, CONR$^{C11}$R$^{C12}$, —NR$^{C11}$SO$_2$R$^{C12}$, —NR$^{C11}$COR$^{C12}$, (C$_0$-C$_3$)alkyl-NR$^{C11}$R$^{C12}$, (C$_1$-C$_3$)alkylCOR$^{C11}$, (C$_0$-C$_6$)alkyl-CO-OR$^{C11}$, cyano, (C$_1$-C$_6$)alkyl-cycloalkyl, phenyl, —O(C$_1$-C$_6$)alkylcycloalkyl, —O(C$_1$-C$_6$)alkylaryl, —O(C$_1$-C$_6$)alkylhetero-cyclic, and (C$_1$-C$_6$)alkylaryl;

$R^{C4a}$ is a heterocyclic group which is substituted with 1 to 3 substituent(s) selected independently from (C$_3$-C$_6$)alkyl, (C$_3$-C$_6$)alkenyl, (C$_0$-C$_3$)alkyl-CN, (C$_3$-C$_6$)alkoxy, (C$_1$-C$_6$)alkylalcohol, (C$_3$-C$_6$)haloalkyl, —OCONR$^{C11}$R$^{C12}$, (C$_1$-C$_6$)alkyl NR$^{C11}$R$^{C12}$ [the (C$_1$-C$_6$)alkyl may be substituted with —OR$^{C10}$ ir —C(O)OR$^{C10}$], (C$_0$-C$_6$)alkyl-NR$^{C11}$SO$_2$R$^{C12}$, (C$_0$-C$_6$)alkyl-C(O)NR$^{C11}$R$^{C12}$, (C$_0$-C$_6$)alkyl-NR$^{C11}$C(O)R$^{C12}$, (C$_0$-C$_6$)alkyl-NR$^{C11}$C(O)OR$^{C12}$, (C$_0$-C$_6$)alkyl-NR$^{C11}$CHR$^{C10}$CO$_2$NR$^{C12}$, (C$_0$-C$_6$)alkyl-CO(O)R$^{C11}$, (C$_0$-C$_6$)alkyl-SO$_2$NR$^{C11}$R$^{C12}$, (C$_0$-C$_6$)alkyl-SO$_t$R$^{C11}$, (C$_3$-C$_8$)cycloalkyl, (C$_1$-C$_6$)alkylcycloalkyl, and (C$_0$-C$_6$)alkylheterocyclic [the heterocyclic ring of the (C$_0$-C$_6$)alkylheterocyclic may be substituted with halo, (C$_1$-C$_6$)alkyl, oxo, —CO$_2$R$^{C11}$ or —NR$^{C11}$R$^{C12}$];

$R^{C4b}$ is a group selected from (C$_1$-C$_6$)alkylaryl, (C$_2$-C$_6$)alkenylaryl, (C$_2$-C$_6$)alkynylaryl, (C$_1$-C$_6$)alkylheterocyclic, (C$_2$-C$_6$)alkenylheterocyclic, (C$_1$-C$_6$)alkylcycloalkyl and (C$_1$-C$_6$)alkyl-O—(C$_1$-C$_6$)alkylaryl, and the cycloalkyl, the aryl and the heterocyclic may be substituted with 1 to 3 substituent(s) selected independently from hydroxyl, oxo, —S(C$_1$-C$_6$)alkyl, (C$_1$-C$_6$)alkyl, (C$_2$-C$_6$)alkenyl, (C$_2$-C$_6$)alkynyl, (C$_1$-C$_6$)haloalkyl, a halogen atom, (C$_1$-C$_6$)alkoxy, aryloxy, (C$_2$-C$_6$)alkenyloxy, (C$_1$-C$_6$)haloalkoxyalkyl, (C$_0$-C$_6$)alkyl-NR$^{C11}$R$^{C12}$, —O(C$_1$-C$_6$)alkylaryl, nitro, cyano, (C$_1$-C$_6$)haloalkylalcohol and (C$_1$-C$_6$)alkylalcohol;

$R^{C6}$ is a group selected independently from hydrogen, (C$_1$-C$_6$)alkyl, (C$_2$-C$_6$)alkenyl, hydroxyl, —COR$^{C7}$, (C$_1$-C$_6$)alkoxy, aryloxy, —O(C$_2$-C$_6$)alkenyl, —O(C$_1$-C$_6$)haloalkyl, (C$_1$-C$_6$)alkyl-NR$^{C7}$R$^{C8}$, (C$_3$-C$_8$)cycloalkyl, heterocyclic, aryl, (C$_1$-C$_6$)alkyl-O—C(O)NR$^{C7}$R$^{C8}$, (C$_1$-C$_6$)alkyl-NR$^{C7}$C(O)NR$^{C7}$R$^{C8}$ and (C$_1$-C$_6$)alkylcycloalkyl, $R^{C7}$ and $R^{C8}$ are groups selected independently from hydrogen, (C$_1$-C$_6$)alkyl, (C$_2$-C$_6$)-alkenyl, (C$_2$-C$_6$)alkynyl, —O(C$_1$-C$_6$)alkyl, (C$_1$-C$_6$)haloalkyl, —O-aryl, —O(C$_3$-C$_8$)cycloalkyl, —O-heterocyclic, —NR$^{C7}$R$^{C8}$, (C$_1$-C$_6$)alkylcycloalkyl, —O(C$_1$-C$_6$)alkylcycloalkyl, —O(C$_1$-C$_6$)alkylheterocyclic, (C$_1$-C$_6$)alkylheterocyclic, —O(C$_1$-C$_6$)alkylaryl, (C$_3$-C$_8$)cycloalkyl, heterocyclic, aryl, and (C$_1$-C$_6$)alkylaryl; and the alkyl, the cycloalkyl, the heterocyclic and the aryl may be substituted with 1 to 3 substituent(s) selected independently from hydroxyl, CN, halo, (C$_1$-C$_6$)alkyl, (C$_1$-C$_6$)alkoxy, (C$_1$-C$_6$)haloalkyl and NR$^{C11}$R$^{C12}$; or $R^{C7}$ and $R^{C8}$ may be combined to form a nitrogen-containing heterocyclic ring further containing 0, 1 or 2 heteroatom(s) selected from an oxygen atom, a nitrogen atom and a sulfur atom, and the said nitrogen-containing heterocyclic ring may be substituted with oxo or (C$_1$-C$_6$)alkyl;

$R^{C10}$, $R^{C11}$ and $R^{C12}$ are groups selected independently from hydrogen, (C$_1$-C$_6$)alkyl, (C$_2$-C$_6$)alkenyl, (C$_3$-C$_8$)cycloalkyl, heterocyclic, aryl and (C$_1$-C$_6$)alkylaryl; and the alkyl, the aryl, the cycloalkyl, and the heterocyclic may be substituted with 1 to 3 substituent(s) selected independently from a halogen atom, (C$_1$-C$_6$)alkylheterocyclic, and (C$_1$-C$_6$)haloalkyl; or $R^{C11}$ and $R^{C12}$ may be combined to form a nitrogen-containing heterocyclic ring further containing 0, 1 or 2 heteroatom(s) selected from an oxygen atom, a nitrogen atom and a sulfur atom; and the said nitrogen-containing heterocyclic ring may be substituted with oxo, (C$_1$-C$_6$)alkyl, —COR$^{C7}$, and —SO$_2$R$^{C7}$;

or a pharmaceutically acceptable salt, solvate, enantiomer, racemate, diastereomer or mixture of diastereomers thereof, comprising preparing (2R,4S)-2-ethyl-6-trifluoromethyl-1,2,3,4-tetrahydroquinolin-4-yl-amine or a salt thereof according to the process of claim 1, 2 or 3, and introducing —(CHR$^{C6}$)$_n$—Y$^C$—R$^{C1}$, —R$^{C4a}$ and —R$^{C4b}$ respectively, followed by conversion of the product into a pharmaceutically acceptable salt, solvate, enantiomer, racemate, diastereomer or mixture of diastereomers thereof, if desired.

8. A process for preparing (R)-2-ethyl-6-trifluoromethyl-2,3-dihydro-1H-quinolin-4-one comprising reacting phosphorus pentoxide with (R)-3-(4-trifluoromethyl-phenylamino)-valeric acid.

9. The process of claim 2, 4, 5, 6, 7 or 8, wherein the reaction of phosphorus pentoxide with (R)-3-(4-trifluoromethyl-phenylamino)-valeric acid is carried out in the presence of an organic sulfonic acid or an organic siloxane.

10. The process of claim 9, wherein the organic sulfonic acid or the organic siloxane is methanesulfonic acid.

11. The process of claim 1, 2, 4, 5, 6 or 7, wherein the palladium catalyst is palladium carbon.

12. A process for preparing a compound shown in the general formula I-h:

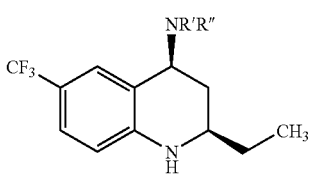

wherein R' and R" are the same or different, and hydrogen or an amino-protecting group, or R' and R" combine together to form an amino-protecting group, comprising asymmetric cyclization reaction of propylidene-(4-trifluoromethyl-phenyl)-amine or an equivalent thereof with an optionally protected vinyl amine shown in the general formula I-g:

wherein the symbols have the same meaning as above, in the presence of an optically active acid catalyst.

13. The process of claim 3, 4, 5, 6, 7 or 12, wherein R' and R" are the same or different, and hydrogen, a tert-butoxycarbonyl group, a benzyloxycarbonyl group, a 9-fluorenylmethyloxycarbonyl group, a 2,2,2-trichloroethoxycarbonyl group, a allyloxy-carbonyl group, a 1-naphthalenemethoxycarbonyl group, a 2-naphthalenemethoxy-carbonyl group, a trifluoroacetyl group, a p-toluenesulfonyl group or a nitrobenzene-sulfonyl group; or R' and R" combine together to form a phthaloyl group.

14. The process of claim 13, wherein R' and R" are the same or different, hydrogen, a benzyloxycarbonyl group, a tert-butoxycarbonyl group, a 1-naphthalenemethoxy-carbonyl group or a 2-naphthalenemethoxycarbonyl group.

15. The process of claim 3, 4, 5, 6, 7 or 12, wherein the optically active acid catalyst is an optically active Lewis acid catalyst.

16. The process of claim 15, wherein the optically active Lewis acid catalyst is a compound comprising a Lewis acidic atom and an optically active ligand selected from a biphenol derivative, a 1,1'-binaphthol derivative or an 1,1'-octahydrobinaphthol derivative.

17. The process of claim 15, wherein the optically active Lewis acid catalyst is a compound comprising an optically active ligand and a Lewis acidic atom, and the optically active ligand is 3,3"-[oxybis(methylene)]bis-(1R,1"R)-1,1'-bi-2-naphthol; (R)-1,1'-binaphthol; (R)-3,3'-dibromo-1,1'-bi-2-naphthol; (R)-6,6'-dibromo-1,1'-bi-2-naphthol; (R)-5,5',6,6',7,7',8,8'-octahydro-bi-2-naphthol; (R)- or (S)-5,5',6,6'-tetramethyl-3,3'-di-tert-butyl-1,1'-biphenyl-2,2'-diol; (R,R)- or (S,S)-1,2-diphenyl-1,2-ethanediol; (1R,2R)- or (1S,2S)-1,2-diphenylethylenediamine; diisopropyl D- or L-tartrate; TADDOL; (R)- or (S)-2-(diphenylhydroxymethyl)pyrrolidine; (R)- or (S)-3-(1H-indol-3-yl)-2-(toluene-4-sulfonylamino)-propionic acid; (R,R)- or (S,S)-2,2'-bis(4-tert-butyl-2-oxazolin-2-yl)propane; (R,R)- or (S,S)-2,2'-bis(4-phenyl-2-oxazolin-2-yl)propane; or (R)- or (S)-2,2'-bis(diphenylphosphino)-1,1'-binaphthyl.

18. The process of claim 15, wherein the optically active Lewis acid catalyst is a compound comprising an optically active ligand and a Lewis acidic atom, and the optically active ligand is 3,3"-[oxybis(methylene)]bis-(1R,1"R)-1,1'-bi-2-naphthol; (R)-1,1'-binaphthol; (R)-3,3'-dibromo-1,1'-bi-2-naphthol; (R)-6,6'-dibromo-1,1'-bi-2-naphthol; (R)-5,5',6,6',7,7',8,8'-octahydro-bi-2-naphthol or (R)-5,5',6,6'-tetramethyl-3,3'-di-tert-butyl-1,1'-biphenyl-2,2'-diol.

19. The process of claim 16, wherein the Lewis acidic atom is boron, aluminum, titanium or ytterbium.

20. (R)-2-ethyl-6-trifluoromethyl-2,3-dihydro-1H-quinolin-4-one.

21. (R)-2-ethyl-6-trifluoromethyl-2,3-dihydro-1H-quinolin-4-one oxime or (R)-2-ethyl-6-trifluoromethyl-2,3-dihydro-1H-quinolin-4-one O-methyl-oxime.

22. The process of claim 17, wherein the Lewis acidic atom is boron, aluminum, titanium or ytterbium.

23. The process of claim 18, wherein the Lewis acidic atom is boron, aluminum, titanium or ytterbium.

* * * * *